(12) United States Patent
Kitching et al.

(10) Patent No.: US 10,011,050 B2
(45) Date of Patent: Jul. 3, 2018

(54) FABRICATION OF AN ORTHODONTIC ALIGNER FROM A NEGATIVE MOLD DESIGNED BY A COMPUTATIONAL DEVICE

(71) Applicant: ORMCO CORPORATION, Orange, CA (US)

(72) Inventors: Ian D. Kitching, Rancho Cucamonga, CA (US); Hua Zhang, San Dimas, CA (US); Tuan A. Do, West Covina, CA (US); Kenneth A. Phelps, Chino Hills, CA (US); Yi-Feng Tsai, Pasadena, CA (US)

(73) Assignee: Ormco Corporation, Orange, CA (US)

( * ) Notice: Subject to any disclaimer, the term of this patent is extended or adjusted under 35 U.S.C. 154(b) by 411 days.

(21) Appl. No.: 14/318,393

(22) Filed: Jun. 27, 2014

(65) Prior Publication Data

US 2014/0315153 A1 Oct. 23, 2014

Related U.S. Application Data

(63) Continuation-in-part of application No. 13/738,513, filed on Jan. 10, 2013, which is a continuation-in-part
(Continued)

(51) Int. Cl.
*B29C 33/38* (2006.01)
*A61C 7/00* (2006.01)
(Continued)

(52) U.S. Cl.
CPC .......... *B29C 33/3842* (2013.01); *A61C 7/002* (2013.01); *A61C 7/08* (2013.01);
(Continued)

(58) Field of Classification Search
None
See application file for complete search history.

(56) References Cited

U.S. PATENT DOCUMENTS 3,502,466 A 3/1970 Vickery
4,844,144 A 7/1989 Murphy et al.
(Continued)

FOREIGN PATENT DOCUMENTS

DE 10 2008 061325 A1 4/2010
EP 2581062 A2 4/2013
(Continued)

OTHER PUBLICATIONS

Yamamoto, K. et al., Optical measurement of Dental Case Profile and Application to Analysis of Three-Dimensional Tooth Movement in Orthodontics, Frontiers of Medical and Biological Engineering, vol. 1, No. 2, pp. 119-130 (1988).
(Continued)

*Primary Examiner* — Benjamin A Schiffman
(74) *Attorney, Agent, or Firm* — Wood Herron & Evans LLP

(57) ABSTRACT

Provided is a method in which a computational device generates a design of a negative mold of teeth. The negative mold of the teeth is fabricated from the design of the negative mold. An aligner is formed using the fabricated negative mold. Provided also is a negative mold of teeth for fabricating a positive model of the teeth for an aligner. The negative mold comprises a tooth surface, and an identity tracking entity coupled to the tooth surface to provide identification.

23 Claims, 24 Drawing Sheets

Related U.S. Application Data of application No. 13/650,886, filed on Oct. 12, 2012, now abandoned.

(60) Provisional application No. 61/546,554, filed on Oct. 12, 2011.

(51) Int. Cl.

| | | |
|---|---|---|
| *A61C 7/08* | (2006.01) | |
| *B33Y 10/00* | (2015.01) | |
| *B29C 64/188* | (2017.01) | |
| *B29C 64/10* | (2017.01) | |
| *A61C 7/36* | (2006.01) | |
| *B29C 64/00* | (2017.01) | |
| *B29C 51/30* | (2006.01) | |
| *B29C 51/00* | (2006.01) | |
| *B29C 51/26* | (2006.01) | |
| *B29C 41/18* | (2006.01) | |
| *B29C 41/02* | (2006.01) | |

(52) U.S. Cl.
CPC ............ *A61C 7/36* (2013.01); *B29C 33/3835* (2013.01); *B29C 33/3878* (2013.01); *B29C 64/00* (2017.08); *B29C 64/10* (2017.08); *B29C 64/188* (2017.08); *B33Y 10/00* (2014.12); *B29C 41/02* (2013.01); *B29C 41/18* (2013.01); *B29C 51/00* (2013.01); *B29C 51/264* (2013.01); *B29C 51/266* (2013.01); *B29C 51/30* (2013.01); *B29C 2033/3871* (2013.01)

(56) References Cited

U.S. PATENT DOCUMENTS

| | | |
|---|---|---|
| 5,131,844 A | 7/1992 | Marinaccio et al. |
| 5,136,515 A | 8/1992 | Helinski |
| 5,139,419 A | 8/1992 | Andreiko et al. |
| 5,368,478 A | 11/1994 | Andreiko et al. |
| 5,395,238 A | 3/1995 | Andreiko et al. |
| 5,431,562 A | 7/1995 | Andreiko et al. |
| 5,447,432 A | 9/1995 | Andreiko et al. |
| 5,454,717 A | 10/1995 | Andreiko et al. |
| RE35,169 E | 3/1996 | Lemchen et al. |
| 5,510,066 A | 4/1996 | Fink et al. |
| 5,512,162 A | 4/1996 | Sachs et al. |
| 5,518,397 A | 5/1996 | Andreiko et al. |
| 5,542,842 A | 8/1996 | Andreiko et al. |
| 5,683,243 A | 11/1997 | Andreiko et al. |
| 5,823,778 A | 10/1998 | Schmitt et al. |
| 5,879,158 A | 3/1999 | Doyle et al. |
| 5,975,893 A | 11/1999 | Chishti et al. |
| 6,015,289 A | 1/2000 | Andreiko et al. |
| 6,200,135 B1 | 3/2001 | Hultgren |
| 6,205,716 B1 | 3/2001 | Peltz |
| 6,210,162 B1 | 4/2001 | Chishti et al. |
| 6,217,334 B1 | 4/2001 | Hultgren |
| 6,227,850 B1 | 5/2001 | Chishti et al. |
| 6,244,861 B1 | 6/2001 | Andreiko et al. |
| 6,322,728 B1 | 11/2001 | Brodkin et al. |
| 6,471,512 B1 | 10/2002 | Sachdeva et al. |
| 6,524,101 B1 | 2/2003 | Phan et al. |
| 6,532,394 B1 | 3/2003 | Earl et al. |
| 6,575,751 B1 | 6/2003 | Lehmann et al. |
| 6,616,444 B2 | 9/2003 | Andreiko et al. |
| 6,846,179 B2 | 1/2005 | Chapouland et al. |
| 7,637,262 B2 | 12/2009 | Bailey |
| 7,641,828 B2 | 1/2010 | DeSimone et al. |
| 7,802,987 B1 | 9/2010 | Phan |
| 2001/0002310 A1 | 5/2001 | Chishti et al. |
| 2002/0006597 A1 | 1/2002 | Andreiko et al. |
| 2003/0003416 A1 | 1/2003 | Chishti et al. |
| 2006/0093982 A1 | 5/2006 | Wen |
| 2006/0177789 A1 | 8/2006 | O'Bryan |
| 2007/0065768 A1 | 3/2007 | Nadav |
| 2008/0138767 A1 | 6/2008 | Kuo et al. |
| 2008/0254402 A1 | 10/2008 | Hilliard |
| 2008/0268400 A1 | 10/2008 | Moss et al. |
| 2009/0029310 A1 | 1/2009 | Pumphrey et al. |
| 2009/0118601 A1 | 5/2009 | Rabolt et al. |
| 2009/0173443 A1* | 7/2009 | Kozlak ............ B29C 67/0062 156/303.1 |
| 2010/0219546 A1* | 9/2010 | Puttler ............... A61C 7/00 264/16 |
| 2011/0039223 A1 | 2/2011 | Li et al. |
| 2011/0165533 A1 | 7/2011 | Li et al. |
| 2012/0183701 A1* | 7/2012 | Pilz ............... B22F 3/1055 427/504 |
| 2013/0029283 A1 | 1/2013 | Matty |
| 2013/0089828 A1 | 4/2013 | Borovinskih et al. |
| 2016/0260001 A1* | 9/2016 | Flores ............ G06K 19/06037 |

FOREIGN PATENT DOCUMENTS

| | | |
|---|---|---|
| JP | 5168654 A | 7/1993 |
| JP | 2009 202033 A | 9/2009 |
| JP | 5253248 B2 | 7/2013 |
| WO | 98/58596 A1 | 12/1998 |
| WO | 99/23973 A1 | 5/1999 |
| WO | 2008047090 A1 | 4/2008 |
| WO | 2009118601 A2 | 10/2009 |
| WO | WO 2011036087 A1 * | 3/2011 ............ B22F 3/1055 |
| WO | 01/47405 A2 | 7/2011 |

OTHER PUBLICATIONS

Crawford, P.R. CAD/CAM in the Dental Office: Does it Work?, Journal, vol. 57, No. 2, pp. 121-123, Feb. 1991.

Biggerstaff, R.H., Computerized Diagnostic Setups and Simulations, The Angle Orthodontist, vol. 40, No. 1, pp. 28-36, Jan. 1978.

European Search Report, related corresponding application No. EP 14 15 0499, dated Apr. 15, 2014.

European Search Report dated Jun. 10, 2015, related to corresponding application No. EP 12188405.0 filed Oct. 12, 2012.

U.S. Patent and Trademark Office, Office Action in U.S. Appl. No. 13/650,886, dated Oct. 9, 2014.

* cited by examiner

FIG. 1 ⌐100

Fabrication of Orthodontic Aligners from Negative Mold generated by a Computational Device ⌐102

Negative mold of tooth generated by rapid prototyping based on the design of a negative mold generated by a computational device

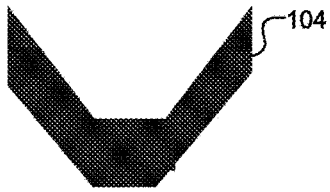
⌐104

⌐106

Positive model made by pouring liquid material (e.g., plaster) into negative mold

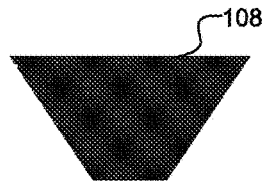
⌐108

⌐110

Portion of aligner generated by thermforming over the positive model

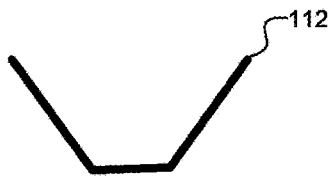
⌐112

FABRICATION OF AN ORTHODONTIC ALIGNER FROM A NEGATIVE MOLD DESIGNED BY A COMPUTATIONAL DEVICE

CROSS-REFERENCE TO RELATED APPLICATIONS

The present application is a continuation-in-part of U.S. patent application Ser. No. 13/738,513 filed on Jan. 10, 2013, wherein U.S. patent application Ser. No. 13/738,513 is a continuation-in-part of U.S. patent application Ser. No. 13/650,886 filed on Oct. 12, 2012, wherein U.S. patent application Ser. No. 13/650,886 claims priority to U.S. Provisional Application No. 61/546,554 filed on Oct. 12, 2011, the disclosure of each of which is hereby incorporated herein by reference in its entirety.

FIELD

The disclosure relates to a system and method for the fabrication of an orthodontic aligner from a negative mold designed by a computational device.

BACKGROUND

Orthodontics is a specialty of dentistry that is concerned with improvement of the general appearance of a patient's teeth and also the correction of malocclusions, crookedness and other flaws of the teeth. Orthodontic braces are devices that are placed on a patient's teeth by a dental practitioner. In an orthodontic brace, wires interact with brackets to move teeth to a desired position. Often, such orthodontic braces are periodically adjusted by the dental practitioner to help align and straighten the teeth. Treatment by the dental practitioner may help in repositioning the teeth to correct flaws and improve the general appearance of the patient.

Another method of orthodontic treatment may use a series of clear, removable teeth aligners as an alternative to orthodontic braces. The series of aligners are successively worn by the patient to reposition the teeth to correct flaws. During a treatment process, a dental practitioner may prescribe a series of aligners, which are generally placed over the patient's teeth, to move one or more teeth from their original position to an aesthetically pleasing position. A series of aligners may be used to treat the patient because the degree of movement produced by an aligner is limited. Each aligner in a series may be designed to move one or more teeth over a portion of the entire distance towards the desired position. An aligner for orthodontic treatment is also referred to as an orthodontic aligner and it is a type of incremental position adjustment dental appliance.

In one mechanism for fabricating aligners, a computer generated design of a series of positive models corresponding to successive positions of a patient's teeth for achieving an aesthetic appearance of the patient's teeth may be generated. The positive model corresponds to a cast of the patient's teeth. The computer generated design may be used by a rapid prototyping mechanism that uses a three-dimensional printer, a stereolithography (SLA) machine, etc., to fabricate a series of positive models. Clear plastic which forms the aligners is molded over the positive models of the tooth configuration via a process referred to as thermoforming. In the thermal brining process a flat thermoplastic sheet is heated and deformed into the desired shape of the orthodontic aligners.

SUMMARY OF THE PREFERRED EMBODIMENTS

Provided is a method in which a computational device generates a design of a negative mold of teeth. The negative mold of the teeth is fabricated from the design of negative mold. An aligner is formed using the fabricated negative mold.

In certain embodiments, the forming of the aligner using the fabricated negative mold further comprises generating a positive model of the teeth from the fabricated negative mold, and thermoforming the aligner over the positive model.

In additional embodiments, the design is a digital data set, and the identification information is associated with the digital data set.

In further embodiments, the fabricating of the negative mold is performed by a rapid prototyping machine. The positive model is generated by pouring material into the negative mold.

In additional embodiments, the negative mold is comprised of an identity tracking surface having an identity tracking entity to provide identification, one or more positioning posts, and at least two accuracy markers.

In certain embodiments, the negative mold is further comprised of a base boundary surface, a rim surface, a mold sitting feature, and a spillway to remove excess poured liquid material that hardens over time to form the positive model.

In additional embodiments, low density build supports are built from a rapid prototyping machine platform to the design platform to support the design platform that supports the pixels of the identity tracking entity.

In further embodiments, the identity tracking entity is selected from a group consisting of a text, a three dimensional barcode, a data matrix and a quick response code.

In yet further embodiments, the identity tracking entity is fabricated as one positive model.

In certain embodiments, the identity tracking entity is fabricated as one negative mold.

In further embodiments, a plurality of identity tracking entities are fabricated to provide redundancy and are coupled to the negative mold.

In yet further embodiments, the identity tracking entity is built as a separate mold and attached to the negative mold.

In certain embodiments, pixel types on the data matrix are spherical, rectangular, or cylindrical, and are spaced adequately and are of a size that satisfies conditions for transference of the data matrix to the positive model.

In further embodiments, pixels on the data matrix and the positioning posts are tapered for retaining the data matrix and the positioning posts on the positive model when the negative mold is separated from the positive model.

In further embodiments, a scanner scans the identification information transferred to the positive model. The scanned identification is printed by a laser marker, on the thermoformed aligner.

In further embodiments, a scanner scans the identification information transferred to the positive model and the thermoformed aligner is trimmed via a laser trimmer.

In certain embodiments, the negative mold does not have a center piece.

In yet additional embodiments, the negative mold has one or more positioning posts to determine position and orientation when the thermoformed aligner is subjected to laser marking and laser trimming, and one or more accuracy markers to determine whether the negative mold has been fabricated with proper dimensions.

In further embodiments, a mold sitting feature supports the negative mold of the teeth.

In certain embodiments, the negative mold is fabricated in a plurality of sections.

In additional embodiments, a plurality of interleaved negative molds that have no center pieces are fabricated by a rapid prototyping machine, wherein the rapid prototyping machine receives the design of the negative mold of the teeth and no design of a positive model of the teeth.

Provided also is a negative mold of teeth for fabricating a positive model of the teeth for an aligner. The negative mold comprises a tooth surface, and an identity tracking entity coupled to the tooth surface to provide identification.

In certain embodiments, a computational device generates a design of the negative mold of the teeth. The negative mold of the teeth is fabricated from the design of the negative mold. A positive model of the teeth is generated from the negative mold, and the aligner is thermoformed over the positive model.

In further embodiments, the negative mold is further comprised of a base boundary surface, a rim surface coupled to the base boundary surface, a mold sitting feature to level the negative mold, a spillway to remove excess poured liquid material that hardens over time, one or more positioning posts to determine position and orientation when the aligner is subjected to laser marking and laser trimming, and one or more accuracy markers to determine whether the negative mold has been fabricated with proper dimensions.

BRIEF DESCRIPTION OF THE DRAWINGS

Referring now to the drawings in which like reference numbers represent corresponding parts throughout:

FIG. 1 illustrates a first block diagram that shows the fabrication of orthodontic aligners from negative molds generated by a computational device, in accordance with certain embodiments;

DETAILED DESCRIPTION

Figure 2:
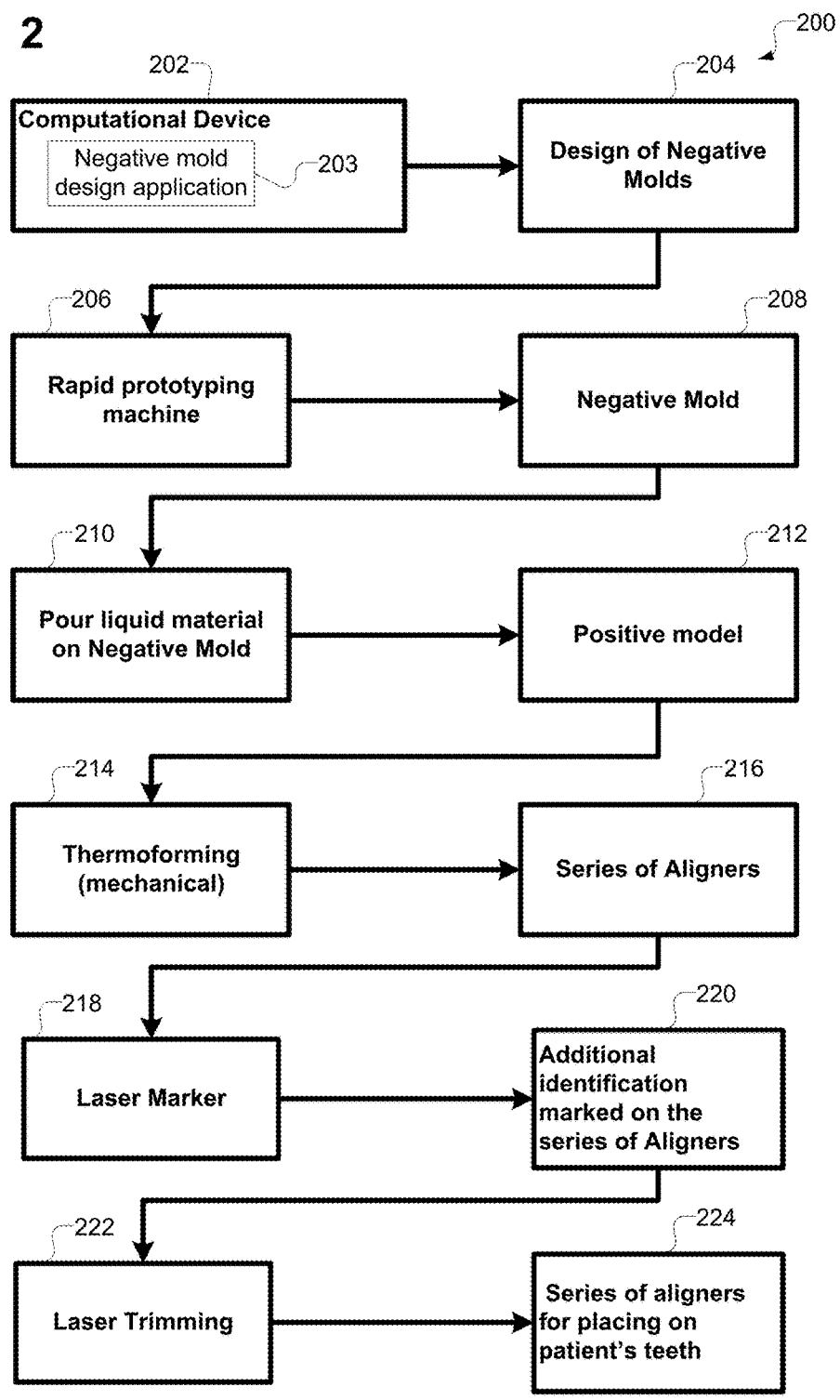
FIG. 2 illustrates a second block diagram that shows the fabrication of orthodontic aligners from negative molds generated by a computational device, in accordance with certain embodiments.

In the following description, reference is made to the accompanying drawings which form a part hereof and which illustrate several embodiments. It is understood that other embodiments may be utilized and structural and operational changes may be made Design of a Negative Mold of Teeth Via a Computation Device In certain embodiments, rather than generating a design of a positive model of teeth, a design of a negative mold of the teeth may be generated by using a computational device. The negative mold is fabricated via a rapid prototyping machine, such as SLA machine, a laser sintering machine, a 3-dimensional printer or via any other type of rapid prototyping mechanism. A positive model of the teeth is made by transforming (e.g., by pouring via automated means, injecting via automated means, or via other automated means) a material (e.g. plaster or certain types of liquid plastic) that hardens over time into the positive model. Subsequently, thermoforming is performed over the positive model of the teeth to fabricate the orthodontic aligners. The positive model corresponds to a cast of the teeth whereas the negative mold corresponds to a mold of the teeth, where a mold may be defined as the negative or hollow cavity produced around a sculpted piece for use in creating multiples of that piece, and a cast may be defined as the positive or a reproduction of the piece. For the purposes of this disclosure the term negative mold corresponds to a mold, and the term positive model corresponds to a cast.

It may be noted that the positive model of the teeth may appear substantially solid and may appear similar to an embossing whereas a negative mold of the teeth may appear hollow and may appear similar to an engraving.

In certain embodiments, the negative mold that is substantially hollow in appearance may use a lesser amount of material than the positive model of the teeth. Since the material deposited for fabricating the mold by rapid prototyping machines is relatively expensive, usage of a lesser amount of material in comparison to the substantially solid positive model may be preferred in certain situations.

Additionally, plaster or plastic that is used to generate the positive model from the negative mold is substantially cheaper than the resin type of material used by the rapid prototyping machines. As a result, the cost of material for generating the negative mold via the rapid prototyping machines and the positive model via plaster or plastic may be less than the cost of material for generating the positive model directly via the rapid prototyping machine.

Generation of negative molds in batches may be much faster in comparison to the generation of positive models via rapid prototyping machines because the negative molds require lesser material to be deposited by the rapid prototyping machines. Therefore the rapid prototyping machines are used more efficiently.

Additionally, clearer aligners may be made with the two step process of generating a negative resin mold via a rapid prototyping machine followed by generating a positive model, in comparison to generating the positive resin mold directly via the rapid prototyping machine. Molds built by the rapid prototyping machine have striations caused by the layered deposition process. As a result, the striations may cause jagged grooves in the aligners generated directly from the positive model fabricated by the rapid prototyping machine. Such striations are decreased in the positive model fabricated from the negative mold. As a result, the positive model may be used to generate a relatively smooth surface for the aligners. The smoother the surface of the aligners the lesser may be the likelihood of trapping of food and bacteria between the aligner and the teeth.

Exemplary Embodiments

FIG. 1 illustrates a first block diagram 100 shows the fabrication of orthodontic aligners from the design of negative molds generated by a computational device, in accordance with certain embodiments.

In FIG. 1, block 102 illustrates a negative mold 104 of a tooth generated by rapid prototyping based on the design of a negative mold of the tooth generated by a computational device. While only one tooth is shown schematically, the negative mold may be for an entire or partial upper or lower arch of teeth. The rapid prototyping may be performed by a rapid prototyping machine that deposits resin in layers to form the negative mold.

Once the negative mold 104 has been fabricated, liquid material is poured into the negative mold and the liquid material is allowed to harden. Block 106 shows the positive model 108 that is generated when the hardened material is separated from the negative mold.

Subsequent to generation of the positive model, thermoforming is performed to mold a sheet of clear plastic over the positive model 108, and in block 110 a portion of the aligner 112 generated via the thermoforming is shown.

Therefore, FIG. 1 illustrates certain embodiments in which orthodontic aligners are fabricated first by generating the design of a negative mold of teeth by a computational device. Then the negative mold is fabricated by a rapid prototyping machine, such as SLA machine or a 3-dimensional printer, etc. A positive model is fabricated from the negative mold, and thermoforming is performed to fabricate the orthodontic aligners.

FIG. 2 illustrates a second block diagram 200 of the fabrication of orthodontic aligners from negative molds generated by a computational device, in accordance with certain embodiments.

A computational device 202 is used to generate the design 204 a negative mold. The computational device 202 may comprise any suitable computational device known in the art, such as a personal computer, a server, a mini computer, a mainframe, a laptop computer, a blade computer, a telephony device, etc. The computational device may execute a negative mold design application 203 implemented in software, hardware, or firmware or any combination thereof to generate the design of the negative molds with or without the assistance of an operator.

A rapid prototyping machine 206 may use the design of the negative mold 204 as an input to fabricate a negative mold 208 by depositing a plurality of layers of resin or other types of material to generate the negative mold 208. The rapid prototyping machine may comprise any SLA machine known in the art that uses stereolithography. Instead of an SLA machine a selective laser sintering (SLS) machine or 3-dimensional printing machines may be used to fabricate the negative mold 204.

Liquid material that can harden over time is poured on the negative mold (block 210) to generate the positive model 212. Thermoforming (block 214) is performing to generate a series of aligners 216. Subsequently a laser marker 218 is used to mark additional identification 220 such as tracking information on the series of aligners 216. Laser trimming 222 is performed to trim the marked aligners such that extra surfaces beyond those needed to cover the teeth are removed to generate the series of aligners 224 for placing on the patient's teeth.

Therefore, FIG. 2 shows the fabrication of a series of aligners, by using first a negative molds and then positive models, and subsequently using thermoforming followed by laser marking and laser trimming.

Figure 3:
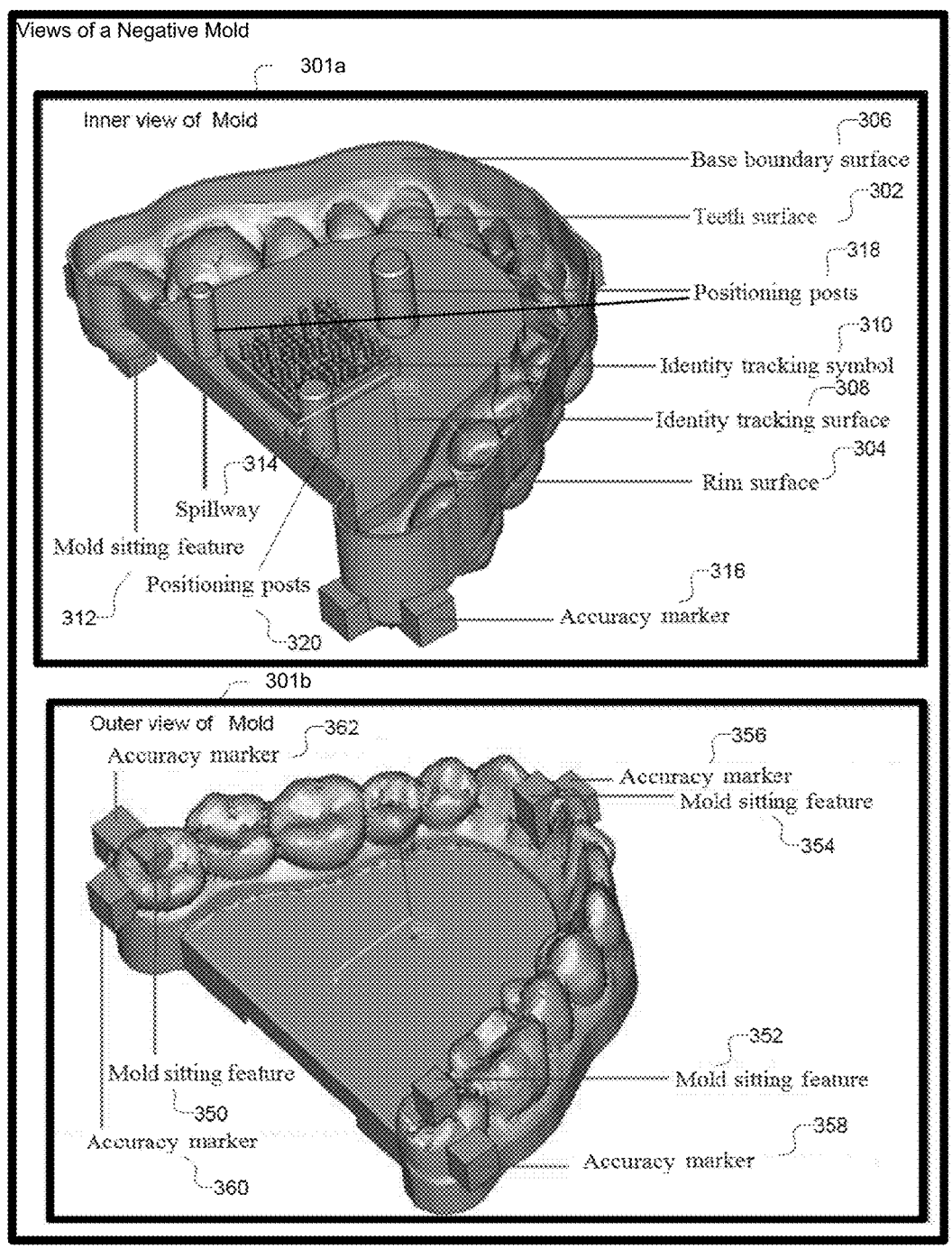
FIG. 3 illustrates views of a negative mold, in accordance with certain embodiments.

FIG. 3 illustrates a block diagram 300 that shows two views 301a, 301b of a negative mold fabricated by a rapid prototyping machine, such as a SLA, SLS, or 3-dimensional printer, in accordance with certain embodiments. View 301a is an inner view of the negative mold that shows the hollow inner surfaces. View 301b is an outer view of the negative mold that shows the outer surfaces. The negative mold of each incremental dental position of the teeth is designed to have some or all of following elements, as shown in at least the inner view 301a of the negative mold in FIG. 3:

(1) Tooth surface 302, which represents incremental positions of the teeth. The tooth surface 302 is fabricated to a relatively high degree of accuracy compared to other surfaces.

(2) Rim surface 304, which is extended from aligner surface boundary. The boundary of the rim surface may be flat on the side that is not connected with the aligner surface 302. The rim length from the flat boundary to the closest aligner boundary point is about 1 mm or it may be parameterized. The flat plane that the rim surface's flat boundary is on, may face any specified direction in space. The rim surface 304 may be created by a rule surface, a sweep surface, an extrusion surface, etc.

(3) Base boundary surface 306, which holds plaster or plastic to create a plaster or plastic base that may provide extra plaster or plastic surface to hold an identity tracking symbol.

(4) Identity tracking surface 308, which may be flat, sloped or any other type of surface. Identity tracking symbols that identify the negative mold may be located on this surface. It is possible to place one or more identity tracking symbols on other surfaces or areas.

(5) Identity tracking symbol 310 comprising a type of identity tracking entity, which represents a unique identification of each aligner. The identity tracking symbol 310 may be a three dimensional data matrix that represents a coded identification, a bar code, a textual, numeric, or graphical identification, etc., as shown in the inner view 301 of the negative mold in FIG. 3. The identity tracking symbol 310 may in other embodiments be a quick response (QR) code. The identity tracking symbol 310 may be used to at least identify the patient for whose teeth the mold is being constructed. Since a plurality of molds for a plurality of patients may be fabricated in a single batch on a rapid prototyping machine, such identification is desirable. The positive model is imprinted with identification based on the identity tracking symbol 310 when the positive model is generated from the negative mold. The identity tracking symbol 310 is used to track each mold and subsequently each plaster or plastic in production. The identity tracking symbol 310 encodes case number, stage number, and arch (lower) or U (upper). The identity tracking symbol 310 is capable of being scanned or read correctly after transfer from mold to plaster or plastic. The identity tracking symbol 310 may be implemented in certain embodiments as a positive model or as a negative mold, whereas the embodiments fabricate a negative mold of the teeth via the rapid prototyping machine. In certain embodiments the identity tracking entity may comprise a radio frequency identification (RFID) tag.

(6) Mold sitting features 312, which are built into the negative mold to ensure the negative mold sits level for pouring plaster or liquid plastic. The mold sitting features are foot-shaped. The outer view 302 shows three mold sitting features 350, 352, 354.

(7) Spillway 314 to direct any excess liquid poured into the negative mold. The spillway 314 may be needed because when liquid is poured into the mold it can spill, causing difficulties while removing the negative mold. The spillway 314 is designed in the negative mold to direct any excess liquid that may have been poured. The width of the spillway 314 may be determined by the flow rate of the liquid that is poured.

(8) Accuracy markers (e.g., 316) are markers of square or any other shape attached to negative mold to measure mold accuracy. The outer view 301b of the negative mold shows four such accuracy positioning or accuracy markers 356, 358, 360, 362. The accuracy markers may be used to determine whether the laser was properly calibrated on the rapid prototyping machine. The positions of the accuracy markers with respect to each other may be determined by measuring distances between them, and if the distances are incorrect a determination may be made that the negative mold has not been fabricated with the proper dimensions probably as a result of an error in fabrication by the rapid prototyping machine because of an improper calibration of the laser. Therefore the accuracy markers allow a checking of the accuracy of the fabrication of the negative molds on the rapid prototyping machine. In certain embodiments the accuracy markers may be placed on the molds of the terminal molar. In certain embodiments accuracy markers are placed only in a first batch and subsequent batches may be manufactured without accuracy markers for a duration of time until checking for recalibration is needed again. Measurements based on the accuracy markers may be performed with calipers, an inspection machine, a coordinate measurement machine (CMM) or via visual inspection, (9) Positioning posts 318, 320 are post like structures resembling cylinders. The inner view 301 of the negative mold shows three such positioning posts of which two are labeled via the reference numeral 318 and the third is labeled via the reference numeral 320. The positioning posts 318, 320 are elements that are used to position the mold such that laser marking and laser trimming may be performed on the aligners. Without the positioning posts 318, 320 the laser marker or the laser trimmer may not be able to determine where to mark identification on the aligners or the location of the gingival margin to trim the aligners. The positioning posts may be used to position and orient the negative mold and positive models as well as the thermoformed aligner for further processing. The posts may be cylindrical, rectangular prism, or any other shape. For laser trimming that removes the gingival areas of the aligners at least two cylindrical positioning posts, or at least one triangular or at least one rectangular post is needed to properly determine the position and orientation of the aligners.

Figure 4:
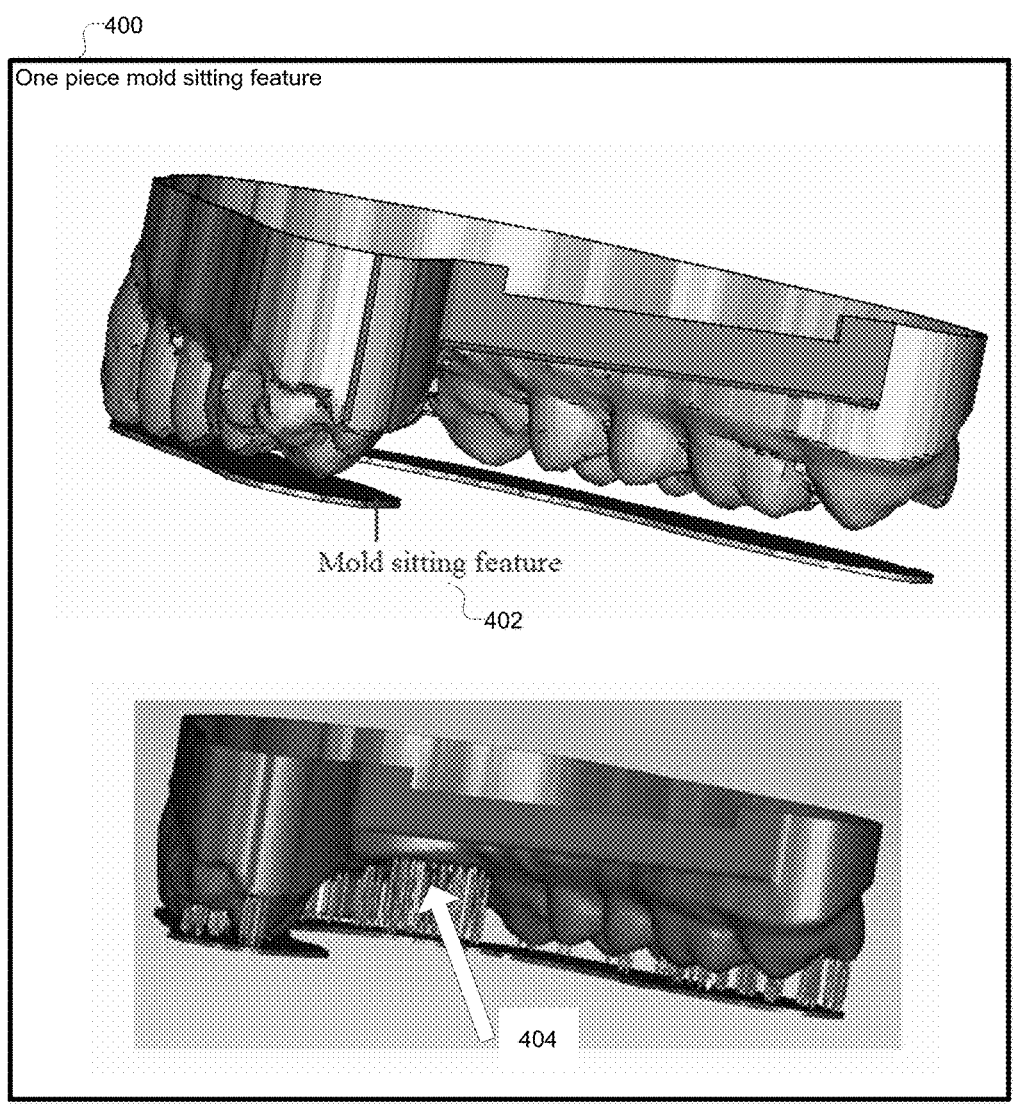
FIG. 4 shows a block diagram that shows a one piece mold sitting feature, in accordance with certain embodiments.

FIG. 4 shows a block diagram 400 that shows a one piece mold sitting feature 402 that is built into the negative mold to ensure that the negative mold site level for pouring liquid. The mold sitting feature 402 is an elongated narrow support layer that is positioned to support the negative molds of the teeth. Fewer support structures are needed for the negative mold on the rapid prototyping machine as a result of the mold sitting feature 402, as shown via the support structures (referred to as build supports) shown via reference numeral 404. Otherwise a significant amount of additional extra resin has to be used by the rapid prototyping machine to generate support structures for the negative mold. The mold sitting feature 402 acts as an additional layer on which the negative mold is built. The mold sitting feature 402 acts like a platform on the bottom of the negative mold undulations and is a narrow support similar in width to the width of the teeth.

The build supports 404 are used to assemble separate mold components into one piece during a rapid prototyping manufacturing process. For a mold designed as shown in FIG. 4, since the sitting sheet (mold sitting features 402) is flat and teeth tips are not on a flat surface, by design, most parts of the sitting sheet is not connected with the crown area of the mold. During the rapid prototyping manufacturing process, supports are built from the upper surface of the sitting sheet to the lower surface of the crown area (FIG. 4 reference numeral 404). These supports connect the two areas together and are strong enough to support crowns during liquid (e.g., plaster) pouring. These supports can become part of the mold by being left on the mold after manufacture.

Figure 5:
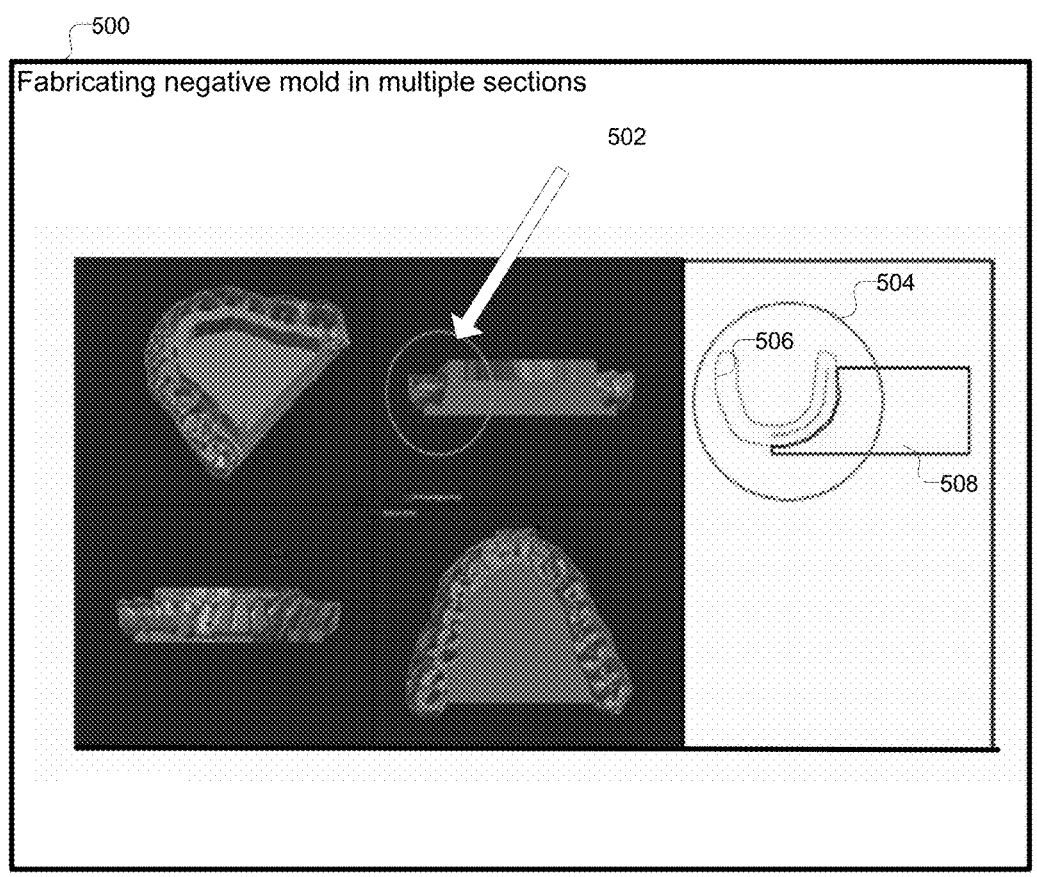
FIG. 5 shows a block diagram of a negative mold that is fabricated in multiple sections and assembled together, in accordance with certain embodiments.

FIG. 5 shows a block diagram 500 of a negative mold that is fabricated in multiple sections and assembled together, in accordance with certain embodiments. For example, an exemplary area 502 is shown magnified in the area 504 to show how two components 506 and 508 are assembled together in an exemplary negative mold.

Figure 6:
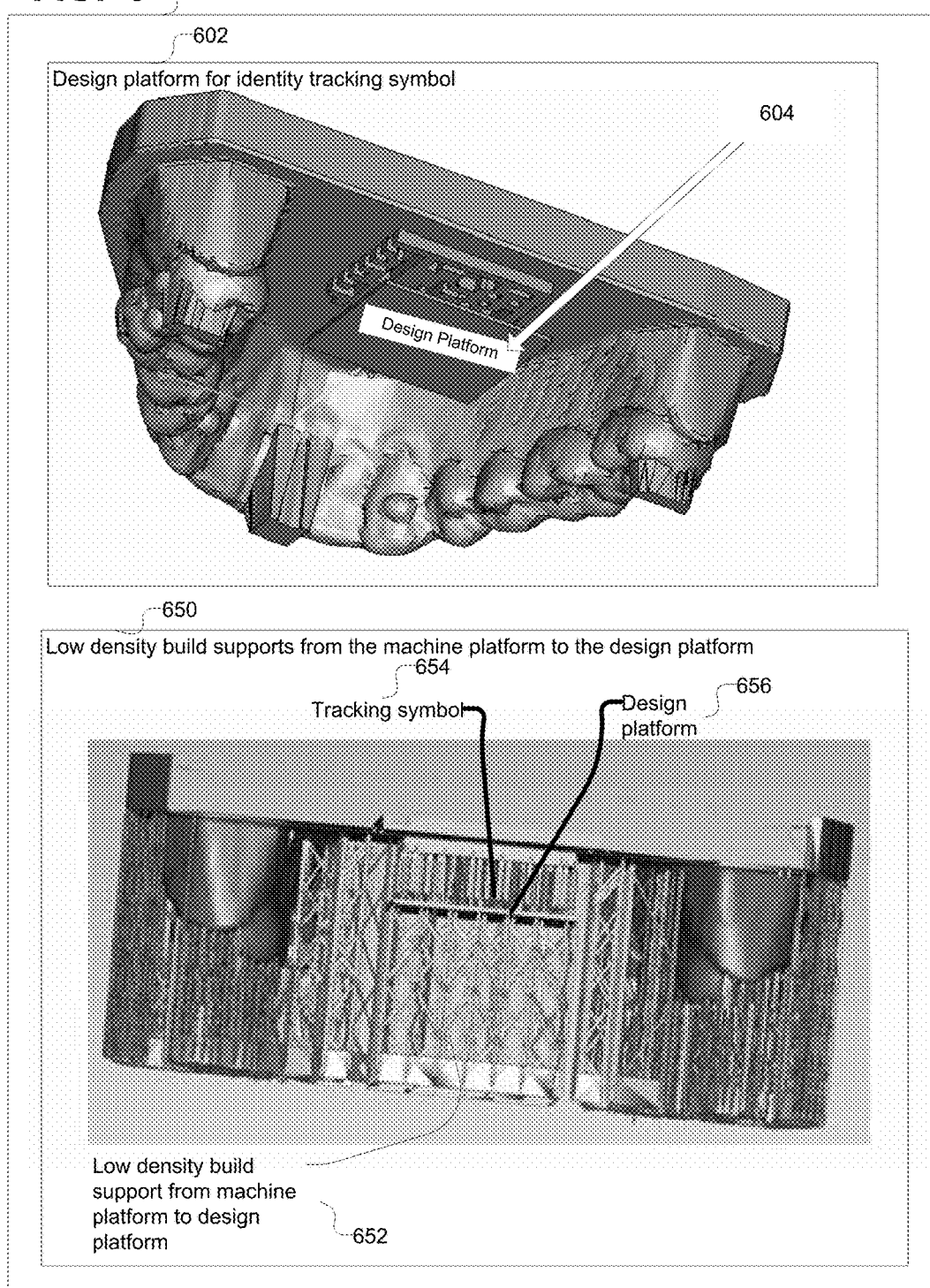
FIG. 6 shows block diagrams of a design platform for the identity tracking symbol and low density build supports, in accordance with certain embodiments.

FIG. 6 shows a block diagram 600 that shows in block 602 a schematic representation of a design platform for the identity tracking symbol and shows in block 650 low density build supports from the machine platform to the design platform, in accordance with certain embodiments.

In block 602, a flat rectangular design platform 604 is shown. The rectangular design platform shown in block 602 is designed by a computational device and is shown floating in space in block 602. The design of the negative mold with the floating design platform 604 is sent from the computational device to the rapid prototyping machine. The design platform 604 allows the identity tracking symbols to be supported with less build support.

Block 650 shows a block diagram of low density build supports 652 for the tracking symbol 654, in accordance with certain embodiments. In certain embodiments, if the tracking symbol 654 faces towards the rapid prototyping machine platform during a rapid phototyping build, then due to its tiny features, high density build supports may be built from the rapid prototyping machine platform to support the tracking symbol, which may result in resin mounding and may stop the rapid prototyping machine. To solve this issue, a thin design platform 656 may be added between the machine platform and the tracking symbol 654, and low density build supports 652 are generated from the machine platform to the thin design platform.

It should be noted that the rapid prototyping machine may automatically determine the density and type of support to build based on the features being supported. The rapid prototyping machine may not put any element is space without fabricating build supports to support the element. The design platform 656 may be supported with relatively low density build supports (i.e., there are relatively fewer build supports) as the design platform 656 is relatively devoid of tiny features and is smooth. Therefore, certain embodiments design the negative mold to reduce the amount of build support by building the design platform to support the tracking symbol.

Figure 7:
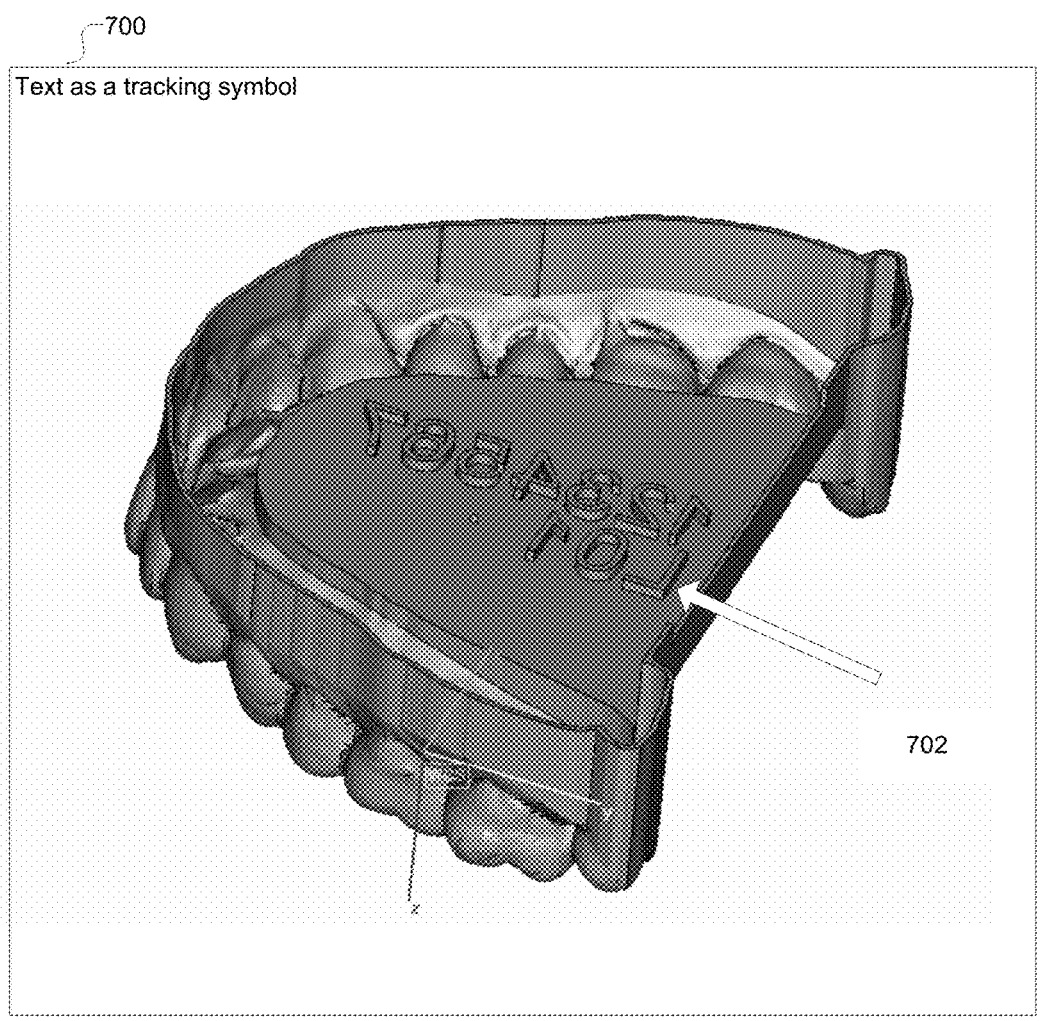
FIG. 7 shows a block diagram that shows a text as an identity tracking symbol, in accordance with certain embodiments.

FIG. 7 shows a block diagram 700 that shows a text 702 as an identity tracking symbol, in accordance with certain embodiments. The text 702 is embossed and so a negative symbol is created on the positive model.

Figure 8:
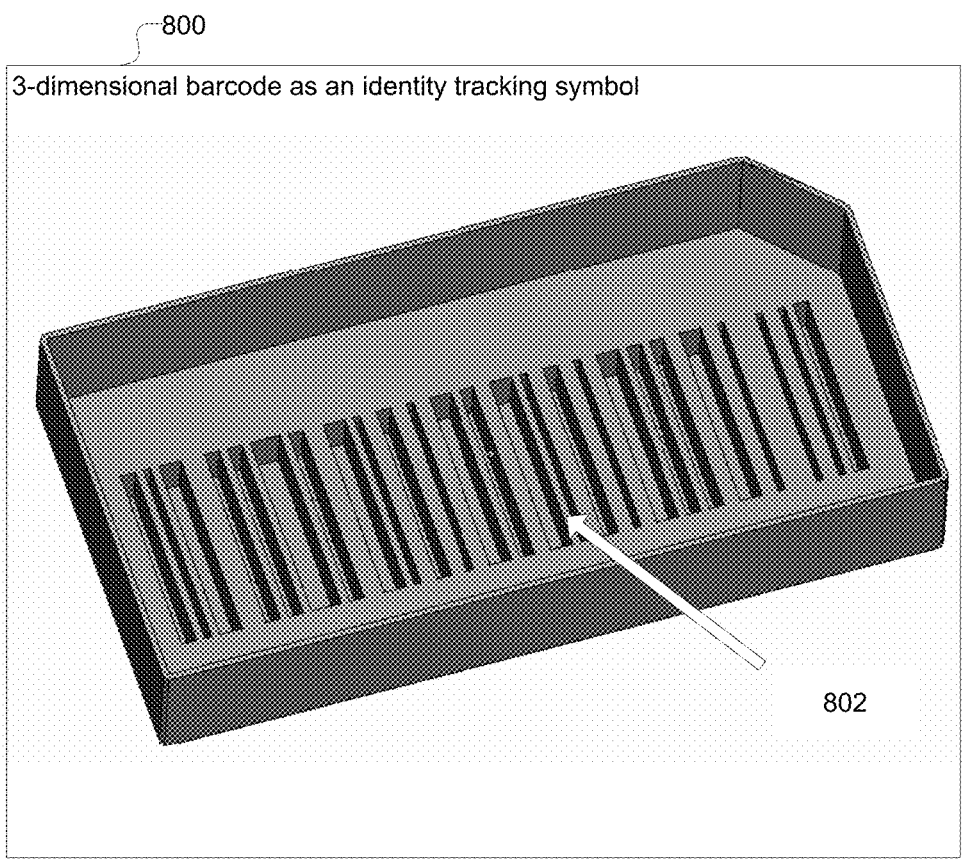
FIG. 8 shows a block diagram that shows a three-dimensional barcode as an identity tracking symbol, in accordance with certain embodiments.

FIG. 8 shows a block diagram 800 that shows a three-dimensional encode 802 as an identity tracking symbol, in accordance with certain embodiments. The barcode 802 is placed as an engraving and so a positive symbol is created on the positive mold.

Figure 9:
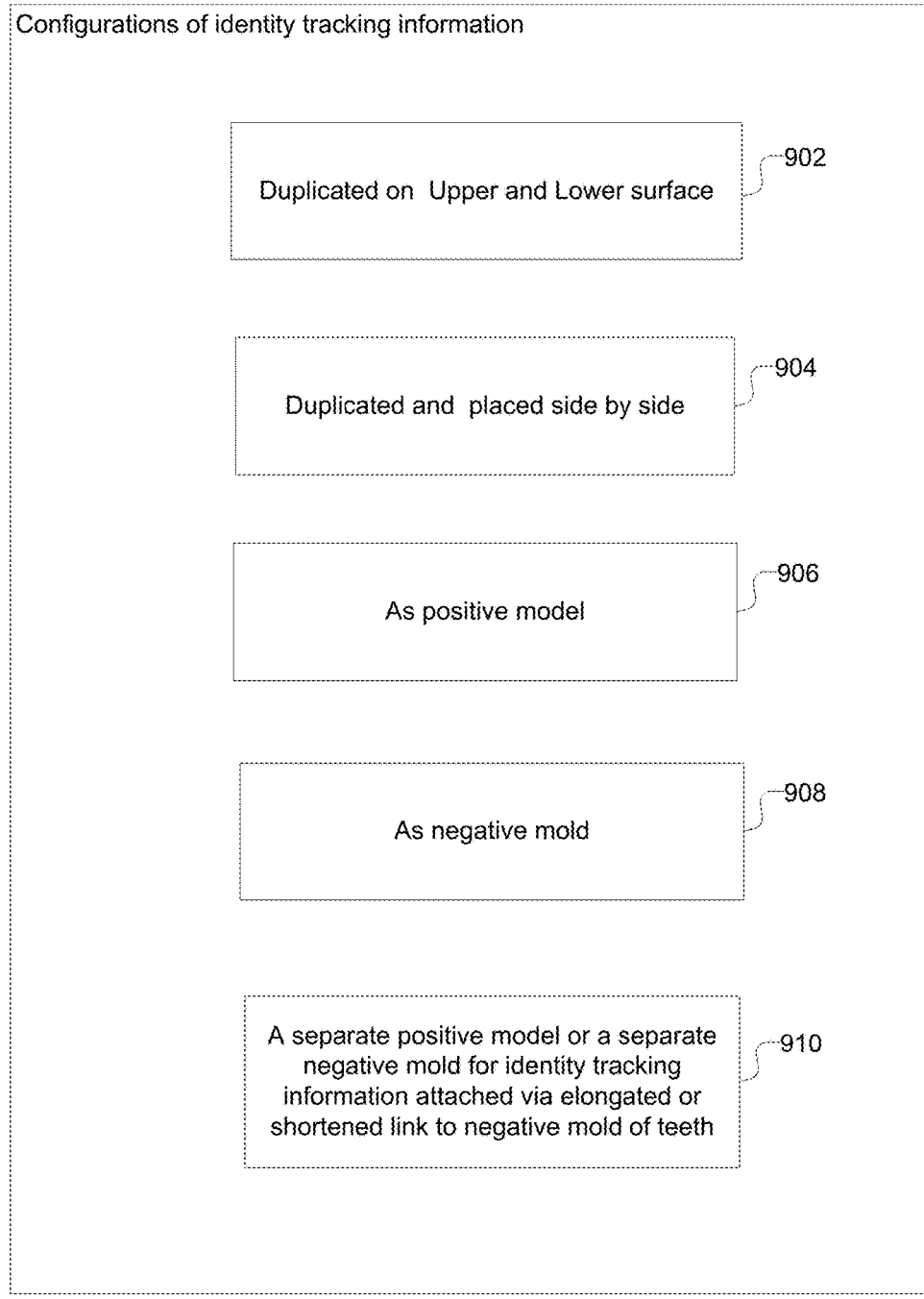
FIG. 9 shows a block diagram of various configurations to identify tracking information, in accordance with certain embodiments.

FIG. 9 shows a block diagram 900 of various configurations to identify tracking information, in accordance with certain embodiments. The identity tracking symbol may be duplicated on both an upper surface and a lower surface (reference numeral 902) or may be duplicated and placed side by side (reference numeral 904), or in some other configuration. In certain embodiments, the identity tracking symbol may be fabricated as a positive model (reference numeral 906) and in other embodiments as a negative mold (reference numeral 908). In certain embodiments if the identity tracking symbol is constructed as a separate negative mold or a separate positive model then it may be attached via an elongated or shortened link to the negative mold of the teeth (reference numeral 910).

Figure 10:
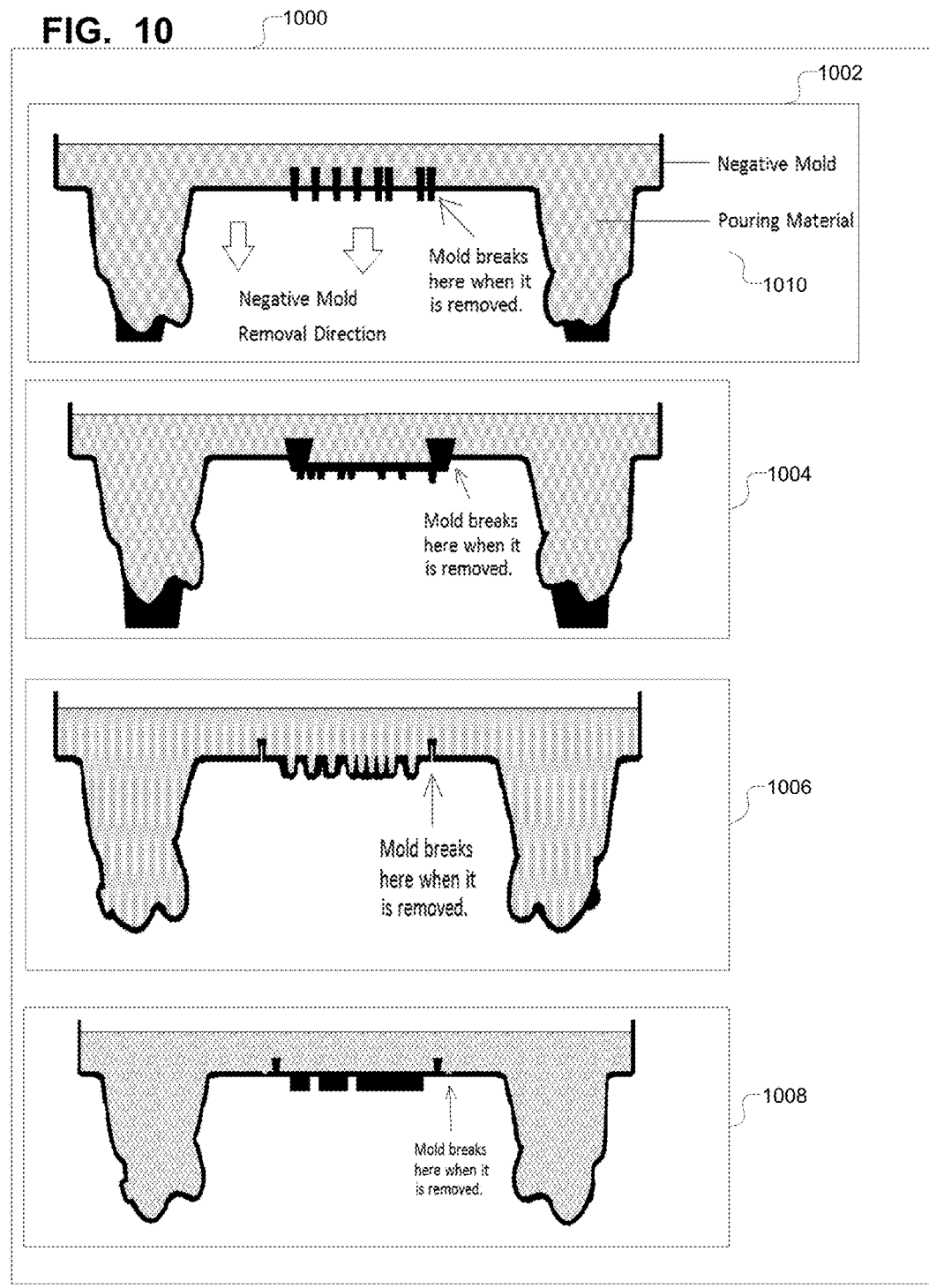
FIG. 10 show the tracking symbol created with various holding features, in accordance with certain embodiments.

FIG. 10 shows a block diagram 1000 that shows tracking symbols created with various holding features, in accordance with certain embodiments. The tracking symbol may be created with holding feet, a separation groove, etc. In certain embodiments, the tracking symbol may be left and secured in plaster or plastic as a resin insert after mold removal.

Block 1002 shows that tapered pixel positions in the pouring material may act as a holding feet to retain pixels on positive model after mold removal. So the pixel portions outside of the pouring material can become a positive matrix on the positive model. Block 1004 shows that the tapered holding feet on the boundary of the data matrix will retain the positive data matrix on positive model after the negative mold is removed. Block 1006 shows that when the negative mold is removed the mold will break at the tapered groove and the pouring material filled data matrix is retained on the positive model as positive data matrix. Block 1008 shows that when the negative mold is removed, the mold will break at the groove and the tapered holding feet will retain the positive data matrix on the positive model. Note that this data matrix is a connected data matrix, not a separate pixels data matrix.

Figure 11:
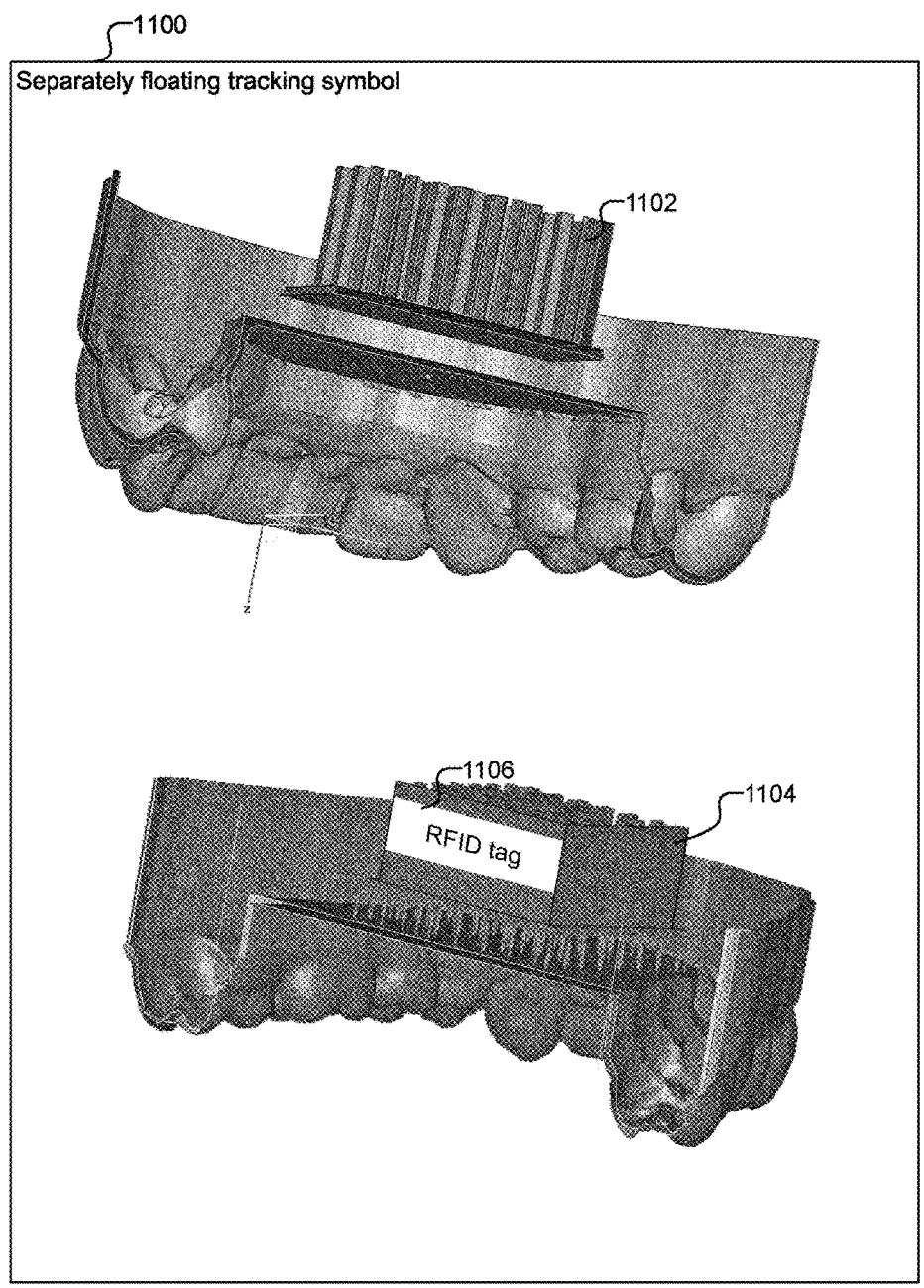
FIG. 11 shows the tracking symbol that is floating and not connected with mold, in accordance with certain embodiments.

FIG. 11 shows a block diagram 1100 with a tracking symbol that is floating and not connected with the negative mold, where the tracking symbol 1102 may subsequently be left and secured in the plaster as an insert. For the mold design as shown in 1102, the final manufactured mold is shown via reference numeral 1104. In certain alternative embodiments instead of a tracking symbol 1102, a Radio-frequency identification (RFID) tag 1106 may be used for identification, or the tracking symbol 1102 may be augmented with the RFID tag 1106. In alternative embodiments, the RFID tag 1106 may be placed in a different location that shown in FIG. 11. RFID readers may send a signal to the RFID tag and read its response for determining the identification. In certain embodiments, the RFID tag 1106 may be programmed to put the identification and other characteristics of the patient for whom aligners are to be manufactured. 125 Khz (low-frequency) tags may be write-once/read-many, and may contain a small unique identification number. 13.56 Mhz (high-frequency) tags are may be read/write, and may typically store about 1 to 2 kilobytes of data in addition to their preset (permanent) unique identification (ID) number. 860-960 Mhz (ultra-high-frequency) tags are typically read/write and may have much larger information storage capacity, in addition to their preset (permanent) unique ID number. RFID tags of other frequencies may be used in alternative embodiments. In certain embodiments read/write RFD tags may be locked to prevent further writing to specific data-blocks in the tag's internal memory, while leaving other blocks unlocked. In certain embodiments the RFID tags may be programmed to store the identification of the patient and other information.

Figure 12:
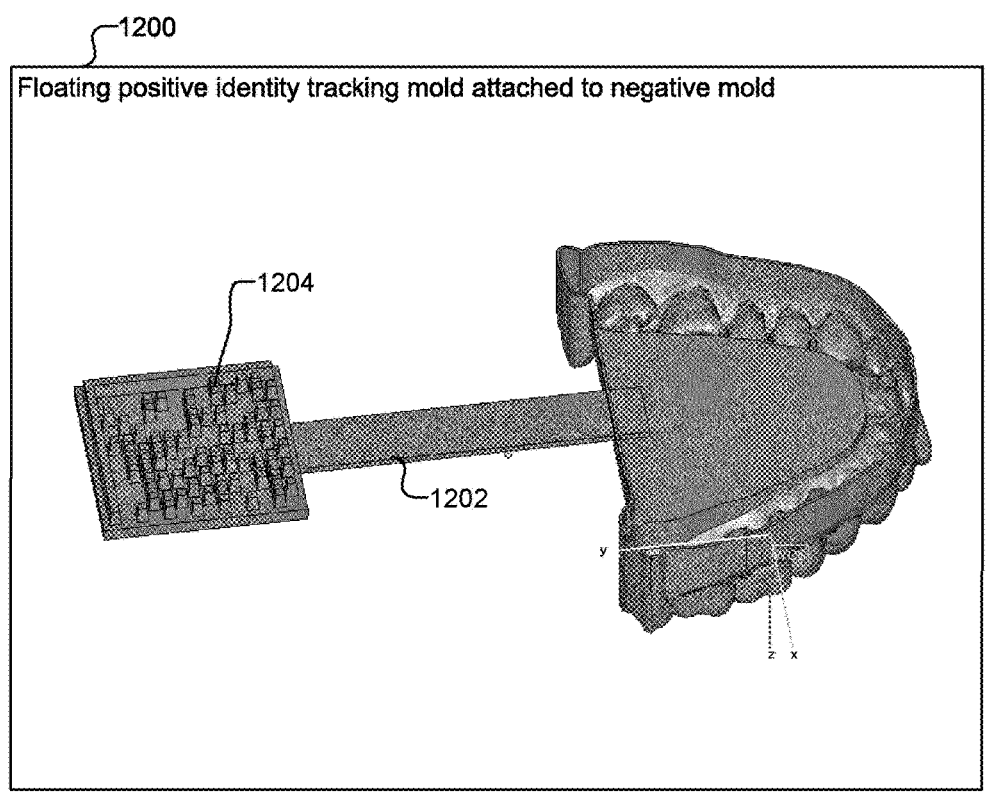
FIG. 12 shows the tracking system as separate but securely attached to the mold by some element, in accordance with certain embodiments.

FIG. 12 shows a block diagram 1200 the tracking symbol 1204 as separate but securely attached to the negative mold by some element 1202, such as a string or a thin plate. The tracking symbol 1204 may be a negative mold or a positive model.

Figure 13:
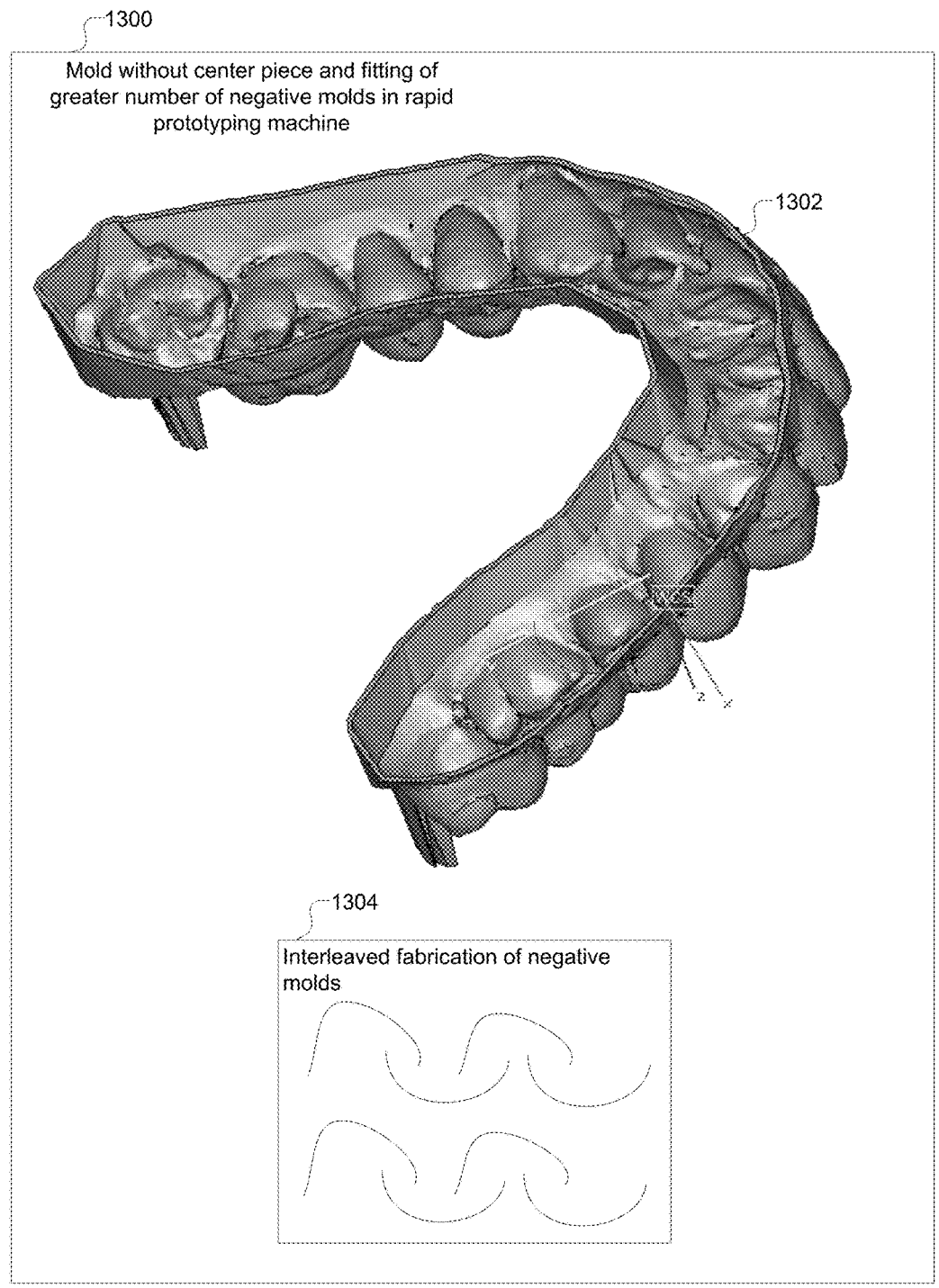
FIG. 13 shows block diagrams of a negative mold with no center piece and interleaving of negative molds, in accordance with certain embodiments.

FIG. 13 shows the block diagram 1300 that shows a negative mold 1302 with no center piece, in accordance with certain embodiments. Such a negative mold 1302 with no center piece may be constructed when a relatively stronger material rather than plaster is used for manufacturing the positive model. Since plaster cracks relatively easily, the center piece is needed in the negative mold to fabricate a positive model made out of plaster. However certain types of plastic if they are poured into the negative mold to generate the positive model, allow the negative mold to be built without the center piece as such plastics are strong and not prone to cracking.

If there is no center piece then many more negative molds may be fabricated on the same tray on a rapid prototyping, machine by fabricating the negative molds in an interleaved pattern as shown via reference numeral 1304. For example, in certain embodiments if there is a center piece then about 100 negative molds may be fabricated on one tray of a rapid prototyping machine but with no center piece about 150 molds may be fabricated on one tray of the rapid prototyping machine.

Figure 14:
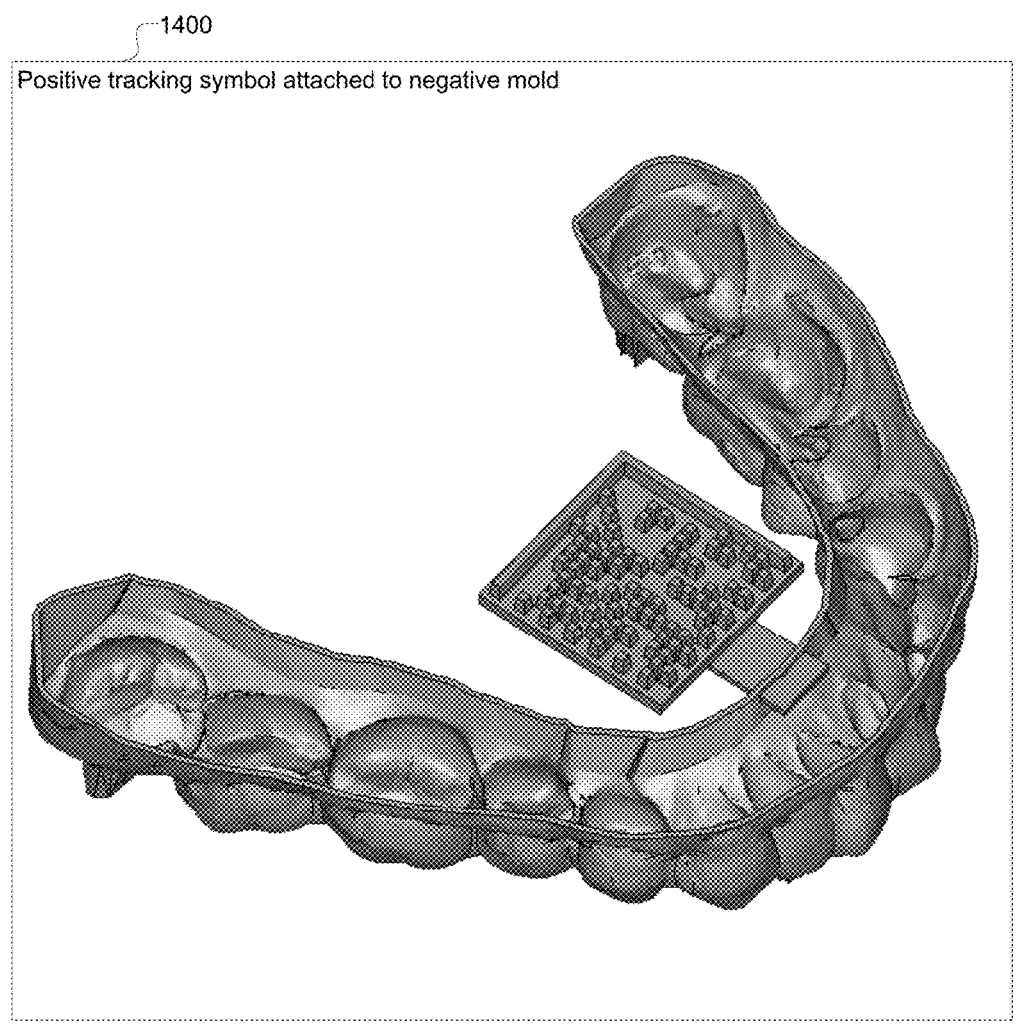
FIG. 14 shows a block diagram of a positive tracking symbol attached to a negative mold, in accordance with certain embodiments.

FIG. 14 shows a block diagram 1400 of an embossed tracking symbol attached to a negative mold. The tracking symbol (e.g., a data matrix) is connected to the negative mold and penetrates into the pouring material, so that when the negative mold is removed, the data matrix remains connected with the positive model made from the pouring material.

Figure 15:
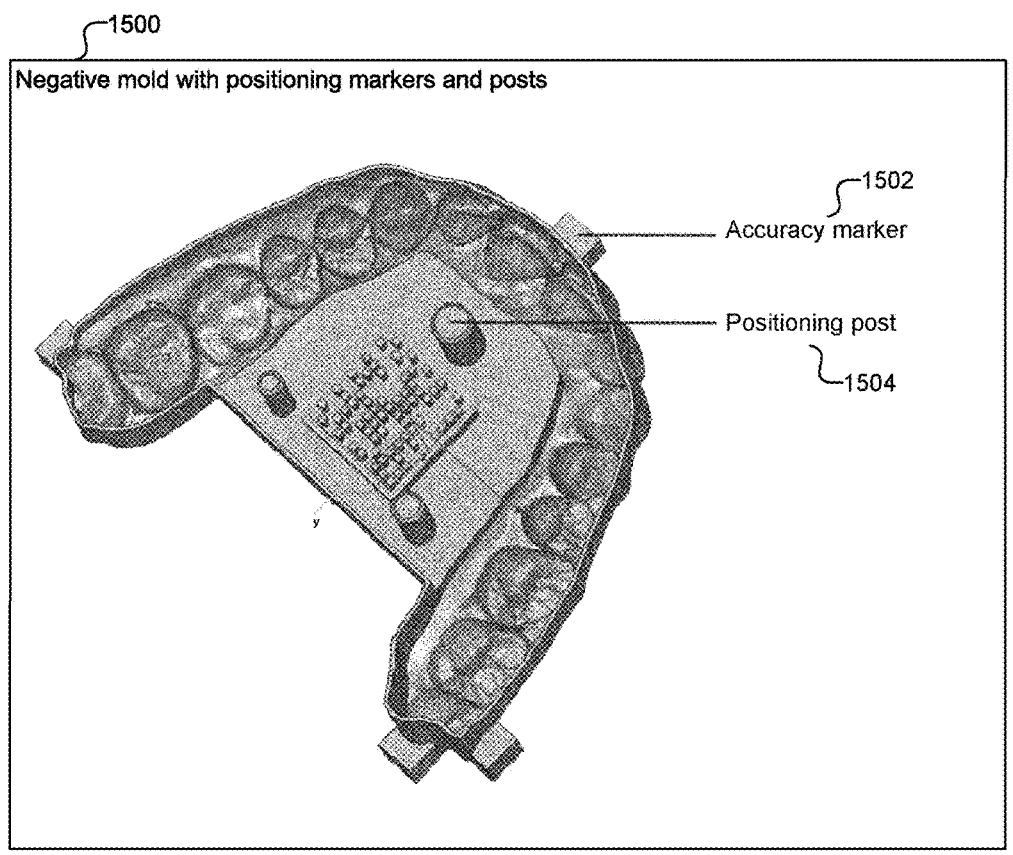
FIG. 15 shows a block diagram that shows accuracy markers and positioning posts on a negative mold, in accordance with certain embodiments.

FIG. 15 shows a block diagram 1500 that shows accuracy markers 1502 and positioning posts 1504 on a negative mold as was illustrated earlier in FIG. 3. The accuracy markers are markers of square or any other shape attached to the mold to measure mold accuracy. The positioning posts 1504 are elements that are used to position the positive model. The positioning posts may be cylindrical, rectangular prism, prism, or any other shape. For laser trimming that removes the gingival areas of the aligners at least two cylindrical positioning posts, or at least one triangular or rectangular posts are needed to properly determine the position and orientation of the aligners.

In certain embodiments, when the negative mold is designed by a computer the design is made in a three dimensional coordinate system. Similarly, for the laser marker or laser trimmer there is a three dimensional coordinate system. The positioning posts 1504 are used by the laser trimmer and the laser marker to position and orient the thermoformed aligner for printing and trimming.

Figure 16:
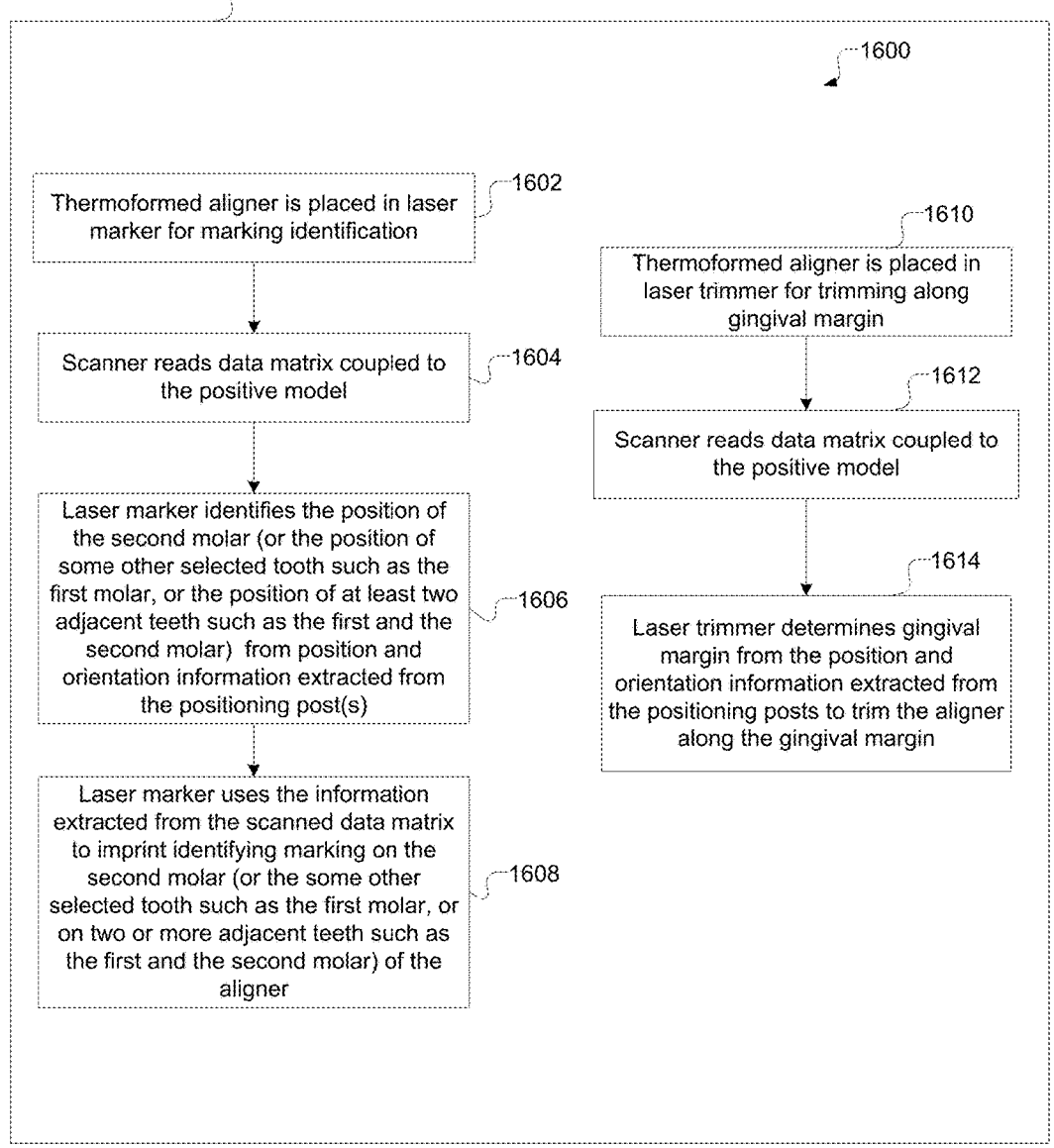
FIG. 16 shows a flowcharts for using a scanner, laser marker, and a laser trimmer for aligner manufacturing from negative molds, in accordance with certain embodiments.

FIG. 16 illustrates a block diagram 1600 that includes two flowcharts, where one flowchart shows operations in which a laser marker imprints identifying marking on one or more teeth, and the other flowchart shows operations for trimming by a laser trimmer, in accordance with certain embodiments.

In one set of operations, control starts at block 1602 in which the thermoformed aligner is placed in a laser marker for marking identification on the aligner. A scanner reads (at block 1604) the data matrix coupled to the positive model. The laser marker identifies (at block 1606) the position of the second molar (or the position of some other selected tooth such as the first molar, or the position of two or more adjacent teeth such as the first and the second molar) from the positioning post(s). The laser marker uses (at block 1608) the information extracted from the scanned data matrix to imprint identifying marking on the second molar (or the some other selected tooth such as the first molar, or the two or more adjacent teeth such as the first and second molar) of the aligner. In certain embodiments for clarity and readability of the identifying marking, the identifying marking is printed over an area that encompasses regions in two adjacent teeth such as the first and the second molar. Also, certain embodiments in which the identifying marking does not fit on one tooth, the identifying marking is printed on more than one teeth. Software medications may indicate the starting position of the identifying marking and the identifying marking may then be printed over one or more than one teeth depending on the length of the identifying marking.

In the other set of operations control starts at block 1610, in which the thermoformed aligner is placed in a laser trimmer for trimming along gingival margin. A scanner reads (at block 1612) the data matrix coupled to the positive modes for identification of the patient. The laser trimmer determines (at block 1614) the gingival margin from the position and orientation information extracted from the positioning post to trim the aligner along the gingival margin by positioning the tool path of the laser trimmer.

As a result of the operations shown in FIG. 16, an aligner imprinted with identifying information where the aligner has been trimmed along the gingival margin is ready for being used on a patient.

Figure 17:
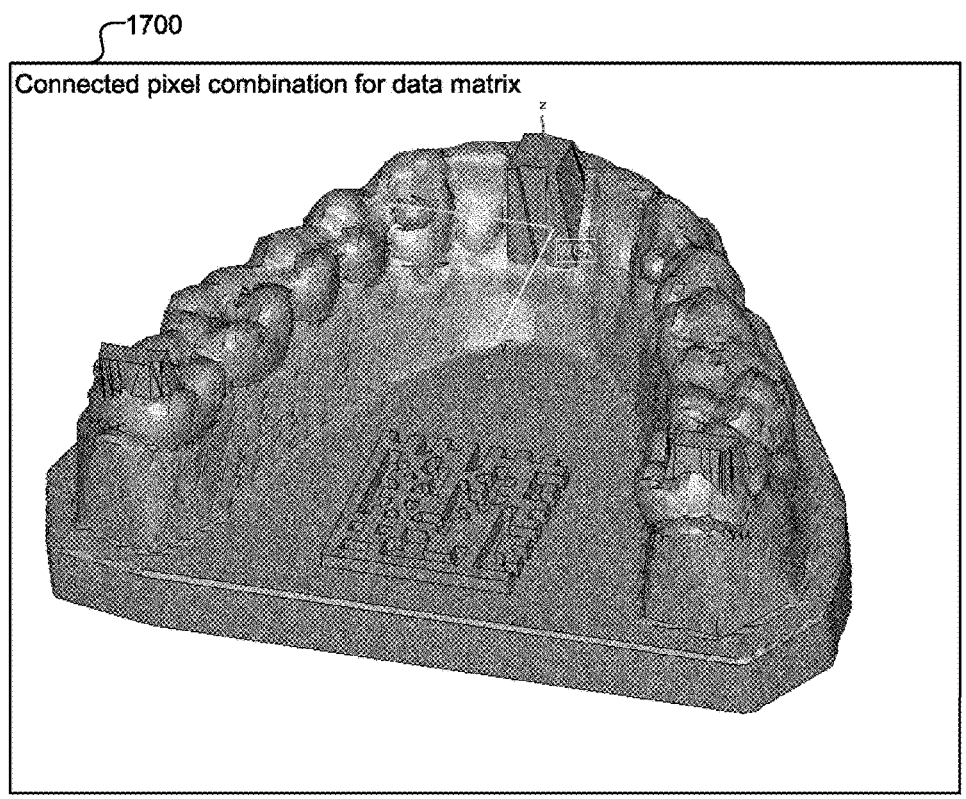
FIG. 17 shows a connected pixel combination for an exemplary data matrix, in accordance with certain embodiments.

FIG. 17 shows a block diagram 1700 of a connected pixel combination for an exemplary data matrix, in accordance with certain embodiments. It may be noted that FIG. 3 showed a separate pixel combination for the data matrix.

Figure 18:
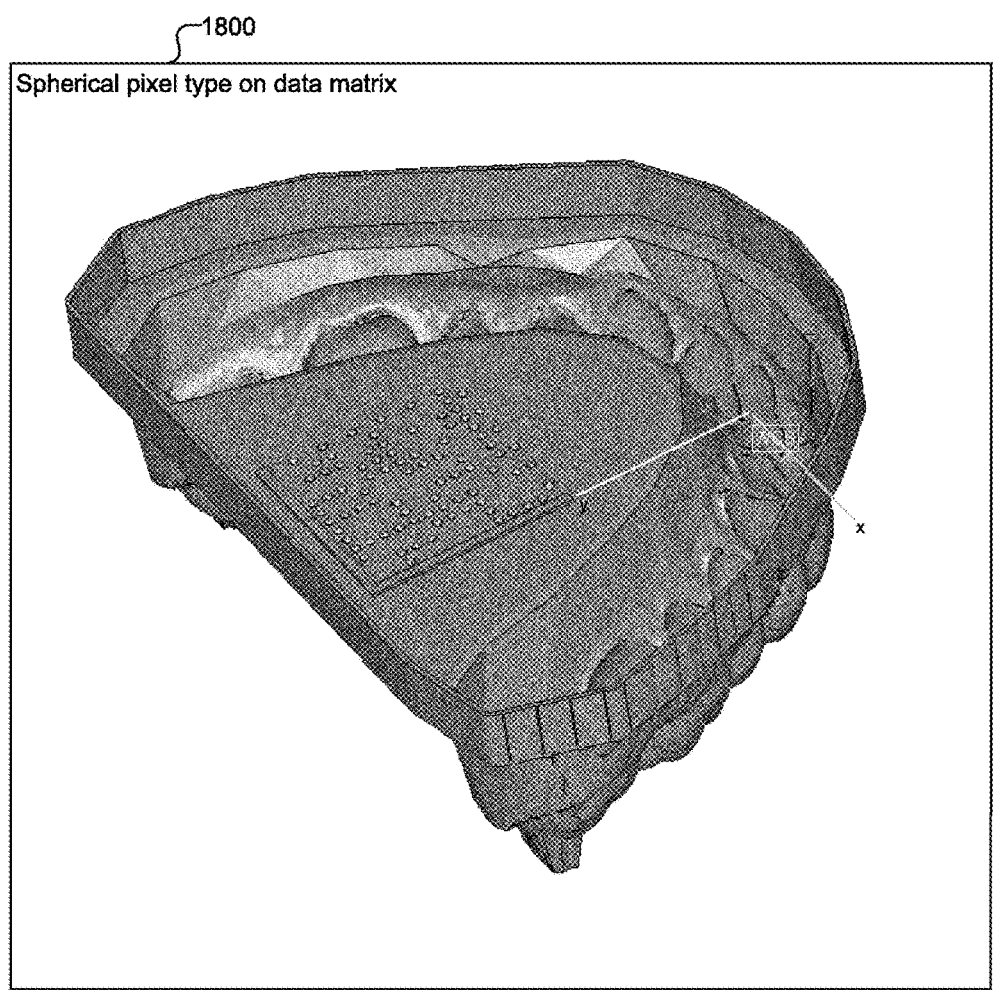
FIG. 18 shows a block diagram of spherical pixel types that form the data matrix, in accordance with certain embodiments.

FIG. 18 shows a block diagram 1800 of spherical pixel types that form the data matrix, in accordance with certain embodiments.

Figure 19:
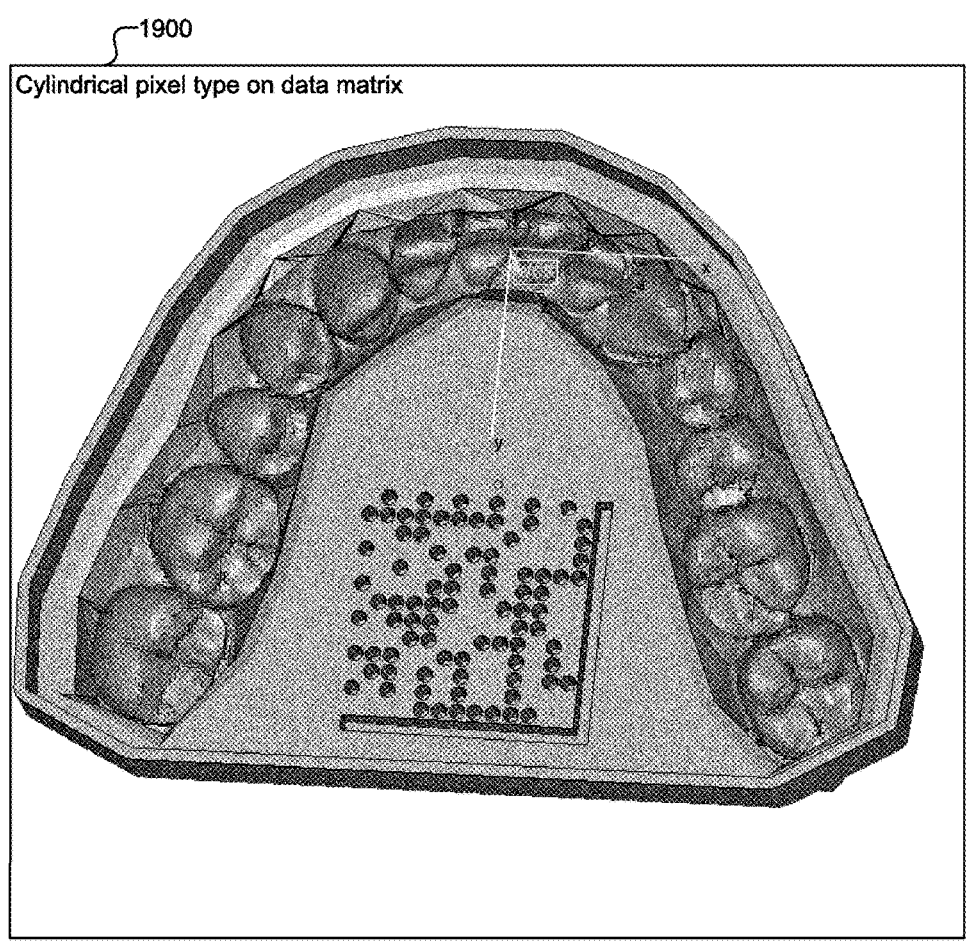
FIG. 19 shows a block diagram of cylindrical pixel types that form the data matrix, in accordance with certain embodiments.

FIG. 19 shows a block diagram 1900 of cylindrical pixel types that form the data matrix, in accordance with certain embodiments. It may be noted that other pixel types, such as square pixels as shown in FIG. 3, may be used to form the data matrix.

In certain embodiments, the pixel size may vary for the data matrix. For example, each pixel may be 1 mm or 1.5 mm in size. The pixel sizes may be large, as long as there is enough space on the mold to put the symbol. The pixel size can be small as long as it is possible to manufacture and pour liquid (e.g., plaster); and the pixels may be read and scanned. There should be adequate spacing between the pixels. All these conditions may be needed for proper transference of the data matrix to the positive model. In certain embodiments, the transference of pixels shaped as rectangular prisms are superior for transference in comparison to other shapes.

In certain embodiments for the data matrix, the pixel taper may be a positive taper (FIG. 12), a negative taper (FIG. 3) or no taper (FIG. 17).

Usually, the tracking symbol needs to have a color contrast with the background to be readable and to be scanned properly. This is accomplished by stenciling or rolling ink of different color from the background color. The ink may be put either on plaster directly or on the mold and then transferred and displayed on plaster. The ink may also be put either on tracking symbol or on background. In certain embodiments, if the mold and the plaster have different color and the tracking symbol is left in the plaster as an insert, the two may have enough color contrast and there may be no need for rolling ink.

If the tracking symbol is positive on plaster and made of plaster, it may not withstand thermoforming and may need to be protected by placing a cover "cup" over the tracking symbol before thermoforming. The cover "cup" may be of any shape and made of any material strong enough to withstand thermoforming.

Figure 20:
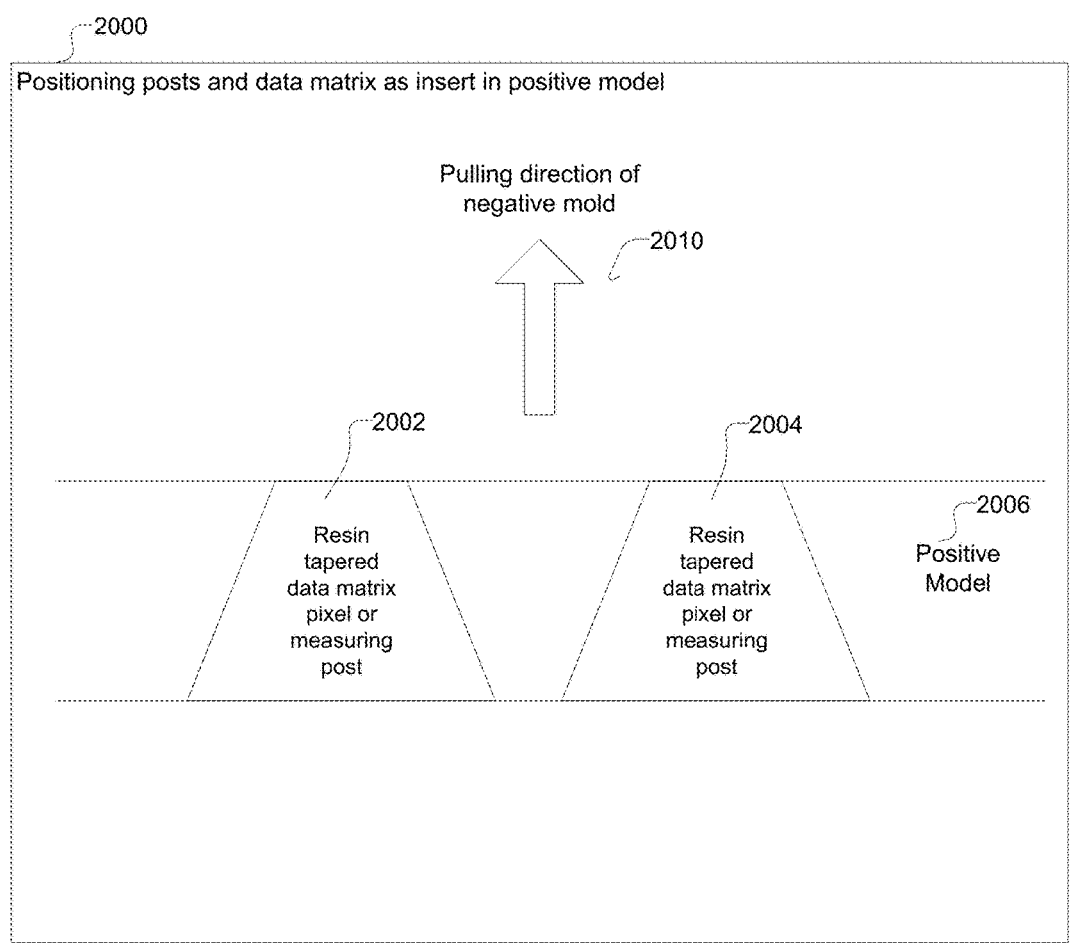
FIG. 20 shows a block diagram of positioning posts and data matrix as inserts in a positive model, in accordance with certain embodiments.

FIG. 20 shows a block diagram 2000 of certain embodiments in which tapered data matrix pixels or positioning posts 2002, 2004 made of resin are left in the positive model 2006 when the negative mold is pulled out in the direction shown via reference numeral 2010.

In such embodiments, the tracking symbols may be separated and tapered 1.0-1.5 mm pixels and combined as a data matrix positive on the mold, resulting as an insert on positive model with ink being painted aver the data matrix on the mold. After mold removal, due to the negative taper, the data matrix is left in the positive model as insert. Protection far thermoforming is not needed. After thermoforming, the data matrix insert in the positive model may be scanned through thermoforming film. This can save the step to cut the film open to scan the data matrix. In a similar manner the positioning posts may also be left in the positive model as an insert.

Figure 21:
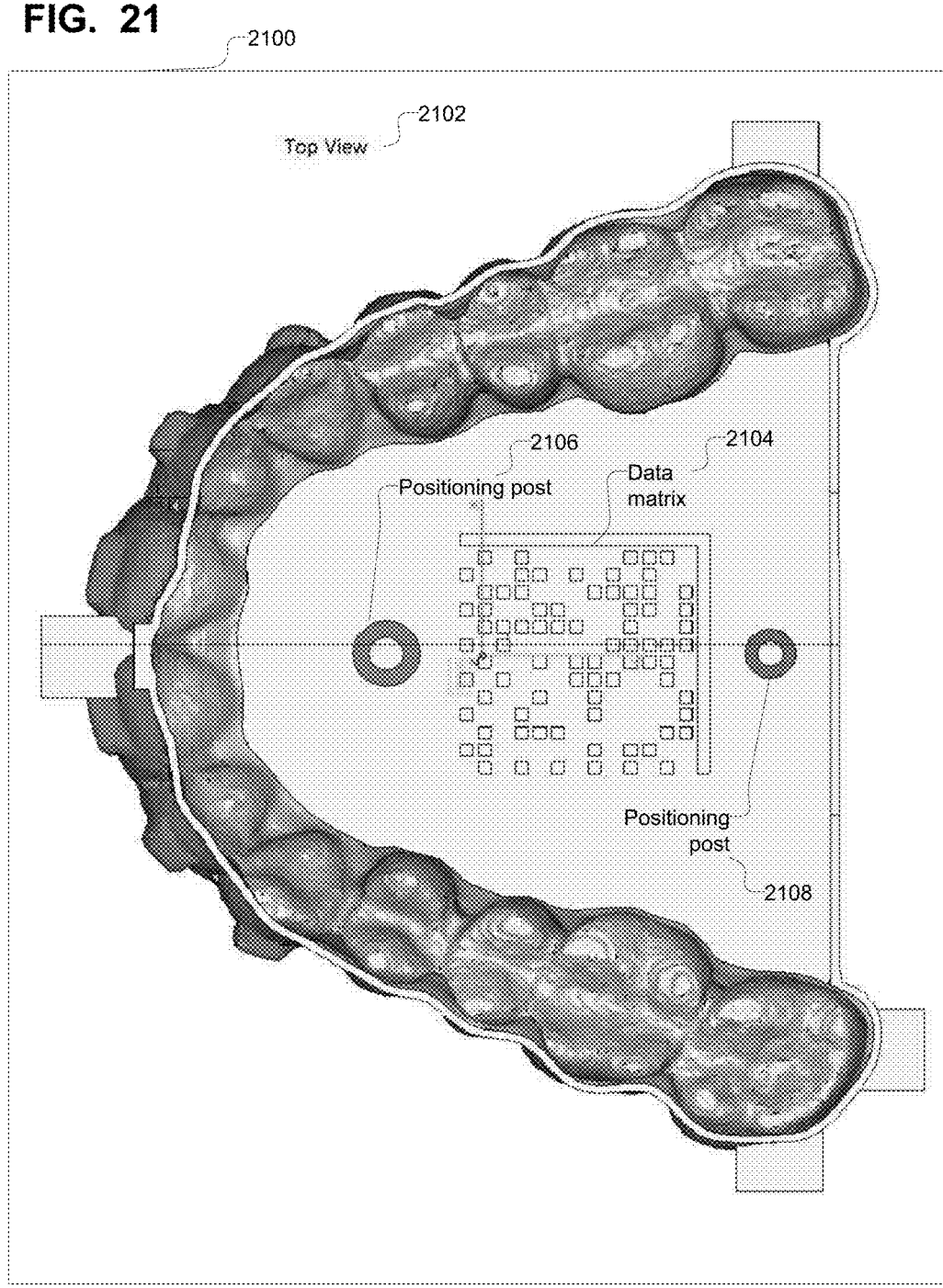
FIG. 21 shows a block diagram of a top view of positioning posts and data matrix, in accordance with certain embodiments.
Figure 22:
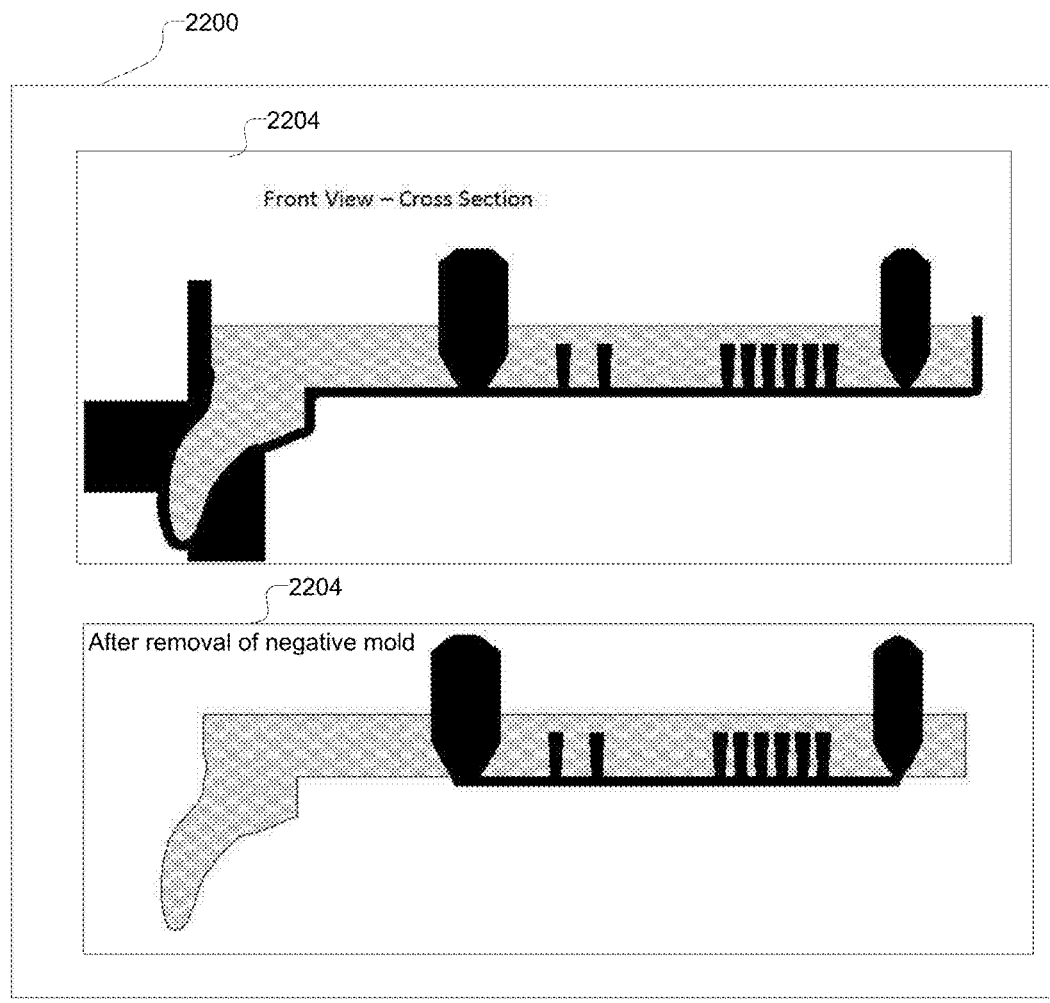
FIG. 22 shows a block diagram of a cross sectional view of positioning posts and data matrix as inserts in a positive model, in accordance with certain embodiments.

To further illustrate certain embodiments shown in FIG. 20, FIG. 21 shows a block diagram 2100 of a top view 2102 of a data matrix 2104 and positioning posts 2106, 2108. FIG. 22 shows in a block diagram 2200, the cross sectional or front view 2204 corresponding to the data matrix 2104 and positional posts 2106, 2108 of FIG. 21. In FIG. 22 after the negative mold is removed (reference numeral 2204), the tapered posts and data matrix pixels are retained in the hardened pouring material as inserts in the positive model.

It may be seen from FIGS. 20, 21, 22 that after the removal of the negative mold, the data matrix may be left in the positive model as an insert.

Figure 23:
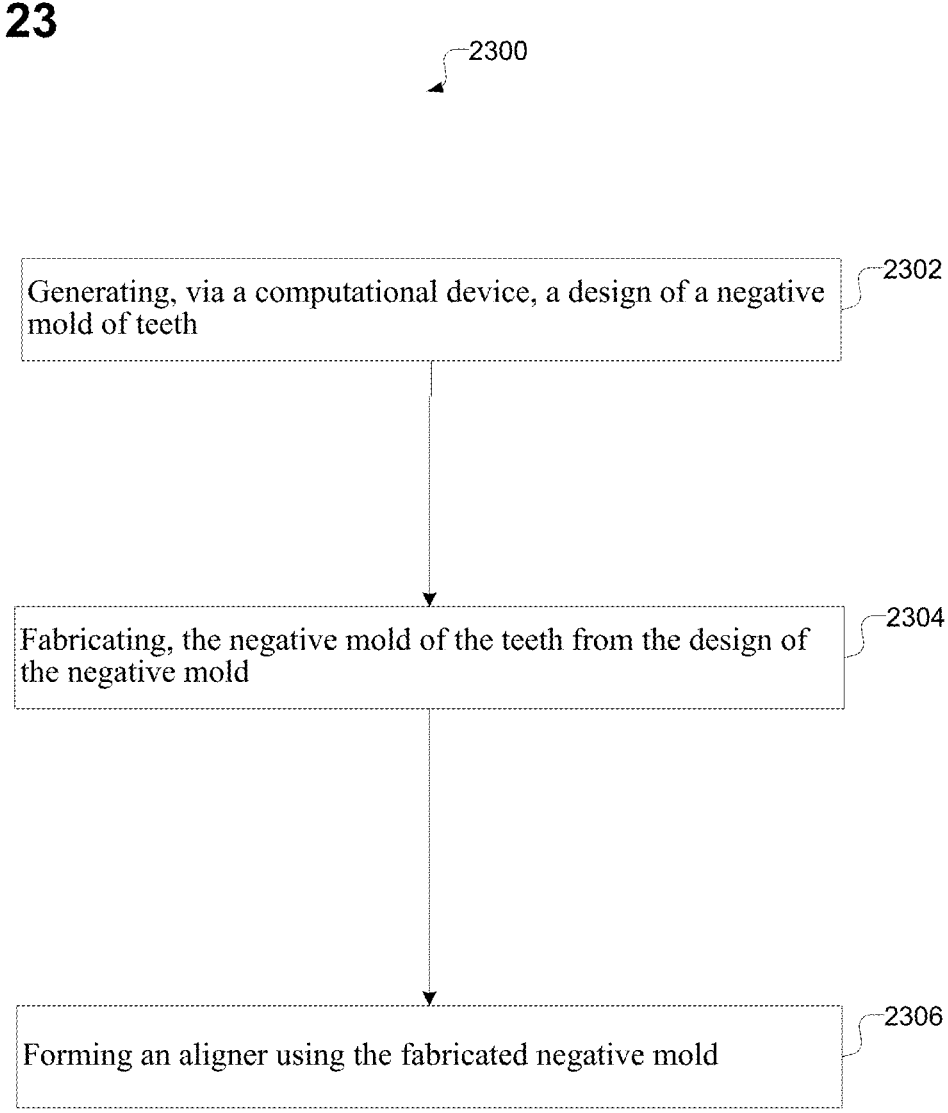
FIG. 23 shows a flowchart of operations performed in accordance with certain embodiments.

FIG. 23 is a flowchart 2300 that shows certain operations performed for forming an aligner. Control starts at block 2302 in which a computational device generates a design of a negative mold of teeth. The negative mold of the teeth is fabricated (at block 2304) from the design of the negative mold. An aligner is formed (at block 2306) using the fabricated negative mold.

Digital Generation of Negative Mold

In certain embodiments, software applications may be designed to generate digital data sets to represent the designed negative mold of each incremental teeth position. Digital mold generation scheme is a combination of general geometry modeling operations, such as cut, clip, flip, extrusion, shelling, Boolean operation, etc. The scheme may be different for different mold designs. Split level approaches and top cavity based approaches may be used for the design of negative molds via the computational device 202.

Physical Manufacturing of Negative Mold

Negative mold may be physically manufactured in different ways by different machines with different materials. Based on experiments on using rapid prototyping technology to produce negative molds it has been determined that plaster surface quality heavily depends on mold's aligner surface quality.

Additionally, while building it is desirable to build the mold "tooth down" to avoid hundreds of support to be built internally within the mold to support the tooth crowns, because build supports within the tooth crowns are difficult to remove entirely and may interfere in the ability to create a precision mold internal surface. In certain embodiments, since the aligner surface is a concave surface, a tiny brush may be used to brush away resin residual after the rapid prototyping process. The accessory geometry features can be designed to improve manufacturability and productivity.

Pouring Plaster into Negative Mold

Plaster or other liquid material is poured into the mold and allowed to harden. Dental plasters vary considerably in their expansion and contraction characteristics but mainly tend to expand. Either expansion or contraction may result in manufactured plaster dimension varying from designed plaster dimension.

For plaster with high expansion/contraction characteristics, an attempt is made to compensate plaster dimension by reducing/enlarging mold dimension from designed plaster dimension.

For plaster with high expansion/contraction characteristics, hollow posts are added internally within the mold to each tooth to reduce plaster expansion/contraction, especially for posterior teeth because due to their mass. The posterior teeth were found to vary significantly more than the anterior teeth.

Experiments snow that by selecting plaster with very low expansion/contraction characteristics, the aligners fabricated from a polyvinyl siloxane (PVS) impression compared to aligners fabricated via rapid prototyping mold and a plaster positive showed less than 50 micron variance.

Removing Negative Mold from Plaster

Mold removal from the plaster was found to be time consuming and in certain situations removed tooth features, such as cusp tips, from the positive model. This problem can be improved by one or combination of several of following methods:

a) Using release agents. Release agents can help to keep plaster from sticking on mold and then being torn off by mold.

b) Design weak points on mold. For example, certain pattern of grooves can be laid out on the outside surface of the mold, which acts like 'perforations', helps to tear apart mold, similar to how dotted lines allow for easier opening of an envelope, c) Heat up mold/plaster. If mold is made of plastics, heating up can soften the mold to help manual removal. Mold should be removed while it is still hot and soft. Otherwise if the mold cools, it may become rigid again and becomes hard to remove or may drag off small plaster pieces. Heating up can be accomplished by:

(i) Boiling water (Shortcoming is that plaster may soak up too much water and become weak and cannot withstand thermoforming).

(ii) High heat oven. Experiments have been done for temperature varying from 135 C to 450 C and heating up time varying from 30 s to 10 minutes. The preferred setting is 416 C for 45 s.

(iii) Extreme high heat. Temperature can be around 1800 degrees F., which can burn the mold off the plaster, but unfortunately the temperature tends to explode the plaster into small pieces as the plaster moisture evaporates with the heat.

(iv) High heat steam. Experiments have been performed using 275 F temperature and heating up for 3 minutes to 15 minutes. A problem is that plaster may soaks up too much water and become weak and cannot withstand thermoforming.

(v) Microwave. Experiments have been done using microwave oven to heat up mold/plaster for 30 s to 3 minutes depending on the power of microwave oven. Heating up by this method is more uniform than ordinary oven.

(vi) Use solvents such as acetone. Immersion in acetone can dissolve plastic mold enough for the mold to come off. Time the mold takes to come off vary from 2 hours to overnight. One problem of this method is that some solvents, such as acetone may dissolve ink painted on mold or plaster which may cause errors in the reading and scanning of tracking symbol, (vii) Use assembly mold. The mold is designed in such a way that each component can be removed piece by piece.

Therefore certain embodiments illustrated in FIGS. 1-23 show how to use a computer designed negative mold to fabricate a negative mold from which a positive model that is a positive model of tooth is generated. The aligners are thermoformed over the positive model.

Additional Embodiments

Certain operations described in the figures may be implemented as a method, apparatus or computer program product using techniques to produce software, firmware, hardware, or any combination thereof. Additionally, certain embodiments may take the form of a computer program product embodied in one or more computer readable storage medium(s) having computer readable program code embodied therein.

A computer readable storage medium may include an electronic, magnetic, optical, electromagnetic, or semiconductor system, apparatus, or device, or any suitable combination of the foregoing. The computer readable storage medium may also comprise an electrical connection having one or more wires, a portable computer diskette or disk, a hard disk, a random access memory (RAM), a read-only memory (ROM), an erasable programmable read-only memory (EPROM or Flash memory), a portable compact disc read-only memory (CD-ROM), an optical storage device, a magnetic storage device, etc. A computer readable storage medium may be any tangible medium that can contain, or store a program for use by or in connection with an instruction execution system, apparatus, or device.

A computer readable signal medium includes a propagated data signal with computer readable program code embodied therein. A computer readable signal medium may be any computer readable medium that is not a computer readable storage medium and that can communicate, propagate, or transport a program for use by or in connection with an instruction execution system, apparatus, or device. The computer readable storage medium is different from the computer readable signal medium.

Computer program code for carrying out operations for aspects of the present invention may be written in any combination of one or more programming languages.

Aspects of the present invention are described below with reference to flowchart illustrations and/or block diagrams of methods, system and computer program products according to certain embodiments. At least certain operations that may have been illustrated in the figures show certain events occurring in a certain order. In alternative embodiments, certain operations may be performed in a different order, modified or removed. Additionally, operations may be added to the above described logic and still conform to the described embodiments. Further, operations described herein may occur sequentially or certain operations may be processed in parallel. Yet further, operations may be performed by a single processing unit or by distributed processing units. Computer program instructions can implement the blocks of the flowchart. These computer program instructions may be provided to a processor of a computer for execution.

Figure 24:
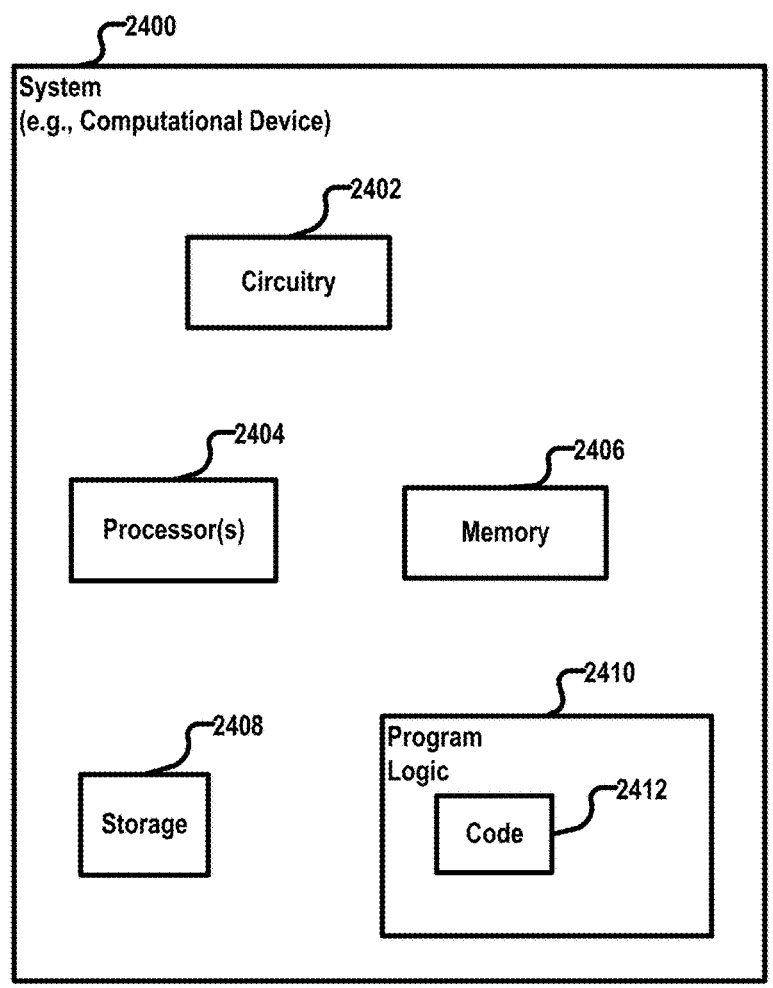
FIG. 24 illustrates a block diagram of a computer system in which the negative mold may be designed, in accordance with certain embodiments.

FIG. 24 illustrates a block diagram of a computer system 2400 (e.g., the computational device 202 shown in FIG. 2) used to design the negative molds 208, in accordance with certain embodiments. In certain embodiments, the computer system 2400 may include a circuitry 2402 that may in certain embodiments include at least a processor 2404. The processor 2404 may comprise any suitable processor known in the art, such as, an arithmetic logical unit, a central processing unit, a circuitry that perform operations, hardware that performs instructions of a computer program, a microprocessor, a parallel processor, an array processor, a vector processor, a transistorized central processing unit, a microcontroller, a logic circuitry, etc. Any device that manipulates digital information based on one or more operational instructions or in a predefined manner is an example of the processor 2404. The system 2400 may also include a memory 2406 (e.g., a volatile memory device), and storage 2408. The storage 2408 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 2408 may comprise an internal storage device, an attached storage device and/or a network accessible storage device. The system 2400 may include a program logic 2410 including code 2412 that may be loaded into the memory 2406 and executed by the processor 2404 or circuitry 2402. In certain embodiments, the program logic 2410 including code 2412 may be stored in the storage 2408. In certain other embodiments, the program logic 2410 may be implemented in the circuitry 2402. Therefore, while FIG. 24 shows the program logic 2410 separately from the other elements, the program logic 2410 may be implemented in the memory 2406 and/or the circuitry 2402.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method of manufacturing an orthodontic aligner for a patient, comprising:
generating, via a computational device, a design of a negative mold of the patient's teeth, the design including a digital data set having identification information to at least identify the patient;
fabricating a negative mold of the patient's teeth from the design with an identity tracking entity, including the identification information, exposed at a surface of the negative mold;
forming an aligner using the fabricated negative mold;
after forming the aligner, scanning the identification information; and
modifying the formed aligner based on the scanned identification information.

2. The method of claim 1, wherein forming the aligner includes:
generating a positive model of the teeth from the fabricated negative mold with the identification information being transferred to the positive model via the identity tracking entity; and
thermoforming the aligner over the positive model.

3. The method of claim 2, wherein the negative mold corresponds to a mold, and the positive model corresponds to a cast.

4. The method of claim 2, wherein the identity tracking entity is a data matrix and pixel types on the data matrix are spherical, rectangular, or cylindrical, and are spaced adequately and are of a size that satisfies conditions for transference of the data matrix from the negative mold to the positive model.

5. The method of claim 2, wherein the identity tracking entity is a data matrix and pixels on the data matrix are tapered for retaining the data matrix on the positive model when the negative mold is separated from the positive model.

6. The method of claim 2, wherein scanning includes scanning, via a scanner, the identification information transferred to the positive model; and modifying includes printing the scanned identification by a laser marker on the thermoformed aligner.

7. The method of claim 2, wherein scanning includes scanning, via a scanner, the identification information transferred to the positive model; and modifying includes trimming the thermoformed aligner via a laser trimmer.

8. The method of claim 2, wherein the negative mold has one or more positioning posts to determine position and orientation when the thermoformed aligner is subjected to laser marking and laser trimming, and one or more accuracy markers to determine whether the negative mold has been fabricated with proper dimensions.

9. The method of claim 3, wherein fabricating the negative mold is performed by a rapid prototyping machine; and generating the positive model includes transferring material into the negative mold.

10. The method of claim 9, wherein the negative mold includes one or more positioning posts; and at least two accuracy markers.

11. The method of claim 10, wherein the negative mold further includes
a base boundary surface;
a rim surface;
a mold sitting feature; and
a spillway to remove excess transferred liquid material that hardens over time to form the positive model.

12. The method of claim 10, wherein low density build supports are built from a rapid prototyping machine platform to the design platform to support the design platform that supports pixels of the identity tracking entity.

13. The method of claim 1, wherein the identity tracking entity is selected from a group consisting of a text, a three dimensional barcode, a data matrix, a quick response (QR) code, and a radio frequency identification (RFID) tag.

14. The method of claim 1, wherein the identity tracking entity is fabricated as one positive model.

15. The method of claim 1, wherein the identity tracking entity is fabricated as one negative mold.

16. The method of claim 1, wherein a plurality of identity tracking entities are fabricated to provide redundancy and are coupled to the negative mold.

17. The method of claim 1, wherein the identity tracking entity is built as a separate mold and attached to the negative mold.

18. The method of claim 1, wherein the negative mold does not have a center piece.

19. The method of claim 1, wherein a mold sitting feature supports the negative mold of the teeth.

20. The method of claim 1, the method further comprising:
fabricating the negative mold in a plurality of sections.

21. The method of claim 1, wherein a plurality of interleaved negative molds that have no center pieces are fabricated by a rapid prototyping machine, and wherein the rapid prototyping machine receives the design of the negative mold of the teeth and no design of a positive model of the teeth.

22. The method of claim 1, wherein modifying includes at least one of printing information on the formed aligner based on the scanned identification information and trimming the formed aligner based on the scanned identification information.

23. A method, comprising:
generating, via a computational device, a design of a negative mold of teeth, wherein the design is a digital data set and identification information is associated with the digital data set;
fabricating, by a rapid prototyping machine, the negative mold of the teeth from the design of the negative mold, wherein the negative mold corresponds to a mold and is comprised of an identity tracking entity to provide the identification information; and
generating a positive model of the teeth from the fabricated negative mold by transferring material into the negative mold, wherein the positive model corresponds to a cast and the identity tracking entity is transferred to the positive model; and
thermoforming an aligner over the positive model.

* * * * *